(12) United States Patent
Kudo et al.

(10) Patent No.: US 8,323,659 B2
(45) Date of Patent: Dec. 4, 2012

(54) METHOD FOR DIAGNOSING AND/OR TREATING TUMOR

(75) Inventors: Chie Kudo, Tokyo (JP); Yutaka Kawakami, Tokyo (JP)

(73) Assignee: Keio University, Tokyo (JP)

( * ) Notice: Subject to any disclaimer, the term of this patent is extended or adjusted under 35 U.S.C. 154(b) by 0 days.

(21) Appl. No.: 13/119,645

(22) PCT Filed: Sep. 11, 2009

(86) PCT No.: PCT/JP2009/065955
§ 371 (c)(1), (2), (4) Date: Apr. 26, 2011

(87) PCT Pub. No.: WO2010/032696
PCT Pub. Date: Mar. 25, 2010

(65) Prior Publication Data
US 2011/0217326 A1  Sep. 8, 2011

(30) Foreign Application Priority Data

Sep. 18, 2008 (JP) ................................. 2008-239943

(51) Int. Cl.
| | |
|---|---|
| *A61K 39/21* | (2006.01) |
| *A61K 39/38* | (2006.01) |
| *A61K 39/00* | (2006.01) |
| *A61K 39/12* | (2006.01) |
| *A61K 38/00* | (2006.01) |
| *A61K 38/04* | (2006.01) |
| *C12N 5/00* | (2006.01) |
| *C12N 5/02* | (2006.01) |
| *C12N 15/00* | (2006.01) |

(52) U.S. Cl. ............... 424/187.1; 424/184.1; 424/185.1; 424/186.1; 530/300; 530/328; 435/325; 435/320.1

(58) Field of Classification Search ........................ None
See application file for complete search history.

(56) References Cited

U.S. PATENT DOCUMENTS
2003/0157597 A1 * 8/2003 Raitano et al. ............... 435/69.1

FOREIGN PATENT DOCUMENTS
| | | |
|---|---|---|
| JP | 2004-502407 | 1/2004 |
| JP | 2007-246451 | 9/2007 |
| WO | WO 01/70941 A2 | 9/2001 |
| WO | WO 2006/077941 A1 | 7/2006 |

OTHER PUBLICATIONS

Mangeney et al. The full-length envelope of an HERV-H human endogenous retrovirus has immunosuppressive properties. Journal of General Virology 2001, vol. 82, pp. 2515-2518.*
Shimizu et al. Induction of Tumor-Specific in Vivo Protective Immunity by Immunization With Tumor Antigen-Pulsed Antigen-Presenting Cells. The Journal of Immunology. Feb. 1. 1989, vol. 142. No. 3, 1053-1059.*
Ferrone et al. A clinically relevant mouse model of human multiple myeloma. Blood 2005, vol. 106, pp. 388-389.*
Dermine et al. Vaccine and antibody-directed T cell tumour immunotherapy. Biochimica et Biophysica Acta 2004, vol. 1704, pp. 11-35.*
Romero et al. Therapeutic cancer vaccines based on molecularly defined human tumor antigens. Vaccine 2002, vol. 20, p. A2-A7.*
Tassone et al. A clinically relevant SCID-hu in vivo model of human multiple myeloma. Blood 2005, vol. 106, p. 713-716.*
Choudhury et al. Clinical Results of Vaccine Therapy for Cancer. Advances in Cancer Research 2006, vol. 95, p. 147-202.*
Martelange et al., "Identification on a human sarcoma of two new genes with tumor-specific expression," *Cancer Research* 60:3848-3855 (2000).
Peinado et al., "Snail, ZEB and bHLH factors in tumour progression: an alliance against the epithelial phenotype?," *Nature Reviews | Cancer* 7:415-428 (2007).
Yi et al., "Human endogenous retrovirus HERV-H family in human tissues and cancer cells: expression, identification, and phylogeny," *Cancer Letters* 231:228-239 (2006).
De Parseval et a., "Characterization of the Three HERV-H Proviruses with an Open Envelope Reading Frame Encompassing the Immunosuppressive Domain and Evolutionary History in Primates," *Virology* 279:558-569 (2001).
International Search Report for International Patent Application PCT/JP2009/065955, mailed Dec. 1, 2009.
Jern et al., "Sequence Variability, Gene Structure, and Expression of Full-Length Human Endogenous Retrovirus H," *Journal of Virology* 79(10)6325-6337 (2005).
Lindeskog et al., "Isolation of a Human Endogenous Retroviral HERV-H Element with an Open *env* Reading Frame," *Virology* 258:441-450 (1999).
Mangeney et al., "The Full-Length Envelope of an HERV-H Human Endogenous Retrovirus has Immunosuppressive Properties," *Journal of General Virology* 82:2515-2518 (2001).

* cited by examiner

*Primary Examiner* — Louise Humphrey
(74) *Attorney, Agent, or Firm* — Clark & Elbing LLP

(57) ABSTRACT

An object of the present invention is to provide methods for diagnosing and/or treating tumors using HERV-H env gene or HERV-H env Env protein. Specifically, tumors are diagnosed by detecting expression of HERV-H env gene; and agents for detecting the expression are used as diagnosing agents. Further, tumors are treated by inhibiting function of HERV-H env gene; and agents for inhibiting the function are used as antitumor agents. Furthermore, tumors are treated by administering a peptide having a certain sequence of HERV-H Env protein and the like; and the peptide is used as a cancer vaccine.

5 Claims, 13 Drawing Sheets

A.

B.

| Panc-1 cells | Cellular shape | Snail | | E-cadherin | | Proliferation | | Cellular functions | | |
|---|---|---|---|---|---|---|---|---|---|---|
| | | gene | protein | gene | protein | vitro | vivo | Adhesion | Migration | Invasion |
| Parent | round | +/- | +/- | ++ | +++ | +++ | +++ | +++ | +/- | +/- |
| D6 | spindle/spreading | ++ | + | +++ | + | ++ | ++ | + | + | ++ |
| D10 | spindle/spreading | +++ | ++ | +++ | + | ++ | + | + | +++ | +++ |
| F3 | spindle/spreading | +++ | +++ | + | + | + | + | + | ++ | +++ |
| F5 | spindle/spreading | ++ | ++ | +++ | ++ | ++ | + | + | ++ | ++ |

METHOD FOR DIAGNOSING AND/OR TREATING TUMOR

CROSS-REFERENCE TO RELATED APPLICATIONS

This application is a U.S. National Stage Application of International Patent Application No. PCT/JP2009/065955, filed Sep. 11, 2009, which claims the benefit of Japanese Patent Application No. JP 2008-239943, filed Sep. 18, 2008.

The present application claims the benefit of priority to the Japanese Patent Application No. 2008-239943 filed on Sep. 18, 2008, and the content of this basic application is herein incorporated by reference.

TECHNICAL FIELD

The present invention relates to methods for diagnosing tumor and diagnosing agents to be used therein, as well as methods for treating tumors, and antitumor agents and cancer vaccines to be used therein.

BACKGROUND ART

LTR-like sequences of human endogenous retrovirus (HERV) and other viruses make up as much as 8% of genome DNA. Of 20 or more kinds of HERVs identified in the human genome, most have mutations in gag, pol and env genes. Some of the genes were detected as being expressed in placenta, teratocarcinoma cell lines, tumors derived from germ cells, breast cancer cell lines, etc.

In particular, the HERV-H gene family is the largest group, including about 100 copies of full-length sequences, 800 to 900 copies of sequences with deletion mutations and about 1000 copies of LTR sequences.

In the HERV-H gene family, it has been reported that HERV-H env gene shows high expression in placenta, skeletal muscle, spleen and thymus, whereas no expression was detected in other normal tissues. Its expression is also detected in tumor cell lines derived from wide variety of tissues (Yi, J-M, Kim, H-M, and Kim, H-S (2006) Tumor Letters vol. 231, pp. 228-239).

SUMMARY OF INVENTION

Technical Problem

An object of the present invention is to provide a method for diagnosing and treating tumors using HERV-H env gene or HERV-H env gene product, and more specifically, to provide a method for diagnosing tumors by detecting expression of HERV-H env gene and a diagnosing agent to be used therein, as well as a method for treating tumors by suppressing function of HERV-H env gene and an antitumor agent to be used therein, and a method for treating and/or preventing tumors by administering a peptide having a certain sequence of HERV-H Env protein and a cancer vaccine to be used therein.

Solution to Problem

Snail, a Zinc-finger transcription factor, is a malignant factor of tumors, and it has been known that as the expression level of Snail becomes higher, the tumor comes to be more malignant (Nature Rev Cancer 7, 415-428, 2007).

One reason for this phenomenon is attributed to the fact that Snail regulates the epithelium-mesenchymal transition (EMT) by inhibiting expression of cell adhesion molecules such as E-cadherin. The EMT takes place in the courses of, for example, gastrulation during ontogeny, developmental processes of tissues and organs, repairing processes after loss of normal tissues and cells, metastatic processes of tumor cells, and the like (Nature Rev Tumor 7, 415-428, 2007). Thus, the overexpression of Snail in tumors is considered to facilitate metastasis and invasion of the tumor cells, leading to a malignant transformation of the tumors.

The inventors of the present application intensively studied the mechanism of the EMT due to the overexpression of Snail in tumors, and discovered that the action of Snail involves HERV-H Env protein. Thus, they demonstrated that diagnosis and treatment of tumors are possible by targeting HERV-H env gene and product thereof, leading to the accomplishment of the present invention.

A tumor-diagnosing agent according to the present invention includes a PCR primer pair or an anti-HERV-H Env antibody, capable of detecting expression of HERV-H env gene. The PCR primer pair may have the sequence of SEQ ID NO: 1 or SEQ ID NO: 2. The tumor may be a pancreatic cancer, a colon cancer, melanoma, a lung cancer, leukemia or an esophageal cancer. A tumor-diagnosing kit according to the present invention includes any one of the abovementioned diagnosing agents.

A pharmaceutical composition according to the present invention includes a function-inhibiting substance for inhibiting function of HERV-H env gene. The function-inhibiting substance may inhibit the expression of HERV-H env gene. The function-inhibiting substance may be a siRNA. An antitumor agent according to the present invention includes any one of the abovementioned pharmaceutical compositions.

A peptide according to the present invention has any one of the sequences of SEQ ID NOs: 3 to 5. The antigen-presenting cell according to the present invention is a cell presenting a peptide having any one of SEQ ID NOs: 3 to 5 on its cell surface. A T-cell according to the present invention may be induced by the above-mentioned antigen-presenting cell and be capable of recognizing a tumor cell expressing HERV-H Env antigen. The T-cell may be a cytotoxic T-cell.

A cancer vaccine according to the present invention includes one or more peptides selected from SEQ ID NOs: 3 to 5, an expression vector expressing the peptide(s), any one of the abovementioned antigen-presenting cells, or any one of the abovementioned T-cells. The cancer vaccine may be against a tumor cell expressing Snail protein or HERV-H Env antigen. Also, the cancer vaccine may contain one or more peptides selected from SEQ ID NOs: 3 to 5 and a tumor antigen peptide other than the peptides with SEQ ID NOs: 3 to 5.

A method for treating and/or preventing tumor according to the present invention is a method in which any one of the above-mentioned vaccines is used in a human or a non-human vertebrate.

The HERV-H env gene as used herein refers to the Human endogenous retrovirus H HERV-H/env60 proviral copy clone 734E12 registered under Accession Number AJ289710 (amino acid sequence: SEQ ID NO: 1, nucleotide sequence: SEQ ID NO: 2).

The term "tumor" as used herein means any tumor generically referred to as malignant tumor of any kind of cellular origin, such as cancers derived from epithelium cells, sarcomas derived from non-epithelium cells, blood tumors, and the like.

BRIEF DESCRIPTION OF DRAWINGS

FIG. 1 shows results obtained by examining the expression of the HERV-H env gene by RT-PCR in human normal tissues (A), tumor cell lines (A) and a human progressive colon cancer tissue (B), in one example of the present invention.

FIG. 2 shows a table made by summarizing the phenotypes of Panc-1 cells in which the snail gene was forcibly expressed in one example of the present invention.

FIG. 3 shows the effects of suppression of the HERV-H env gene expression in Panc-1 cells in which the snail gene was forcibly expressed in one example of the present invention.

FIG. 4 presents graphs showing the results obtained by measuring the amounts of gamma interferon produced in genetically modified mice expressing HLA-A24 after the HERV-H Env-specific CTL induced by the HERV-H Env peptide was further stimulated by the HERV-H Env peptide, in one example of the present invention.

[FIG. 5-1]

FIG. 5-1 presents graphs (A and C) showing the results obtained by measuring the ratios of killed tumor cells after tumor cells expressing HERV-H Env were allowed to contact with the HERV-H Env-specific CTL, which had been induced from HLA-A24 positive monocytes isolated from peripheral blood of a healthy individual with the HERV-H Env peptide, in one example of the present invention.

[FIG. 5-2]

FIG. 5-2 presents graphs (B and D) showing the results obtained by measuring the amounts of gamma interferon produced after the HERV-H Env-specific CTL, which had been induced from HLA-A24 positive monocytes isolated from peripheral blood of a healthy individual with the HERV-H Env peptide, was further stimulated with the HERV-H Env peptide in one example of the present invention.

[FIG. 5-3]

FIG. 5-3 presents a graph (E) showing the results obtained by measuring the ratios of killed tumor cells after tumor cells expressing HERV-H Env were allowed to contact with the HERV-H Env-specific CTL, which had been induced from HLA-A02 positive monocytes isolated from peripheral blood of healthy individuals with the HERV-H Env peptide, in one example of the present invention.

FIG. 6 presents a graph showing the result that immunoreactivity was synergistically enhanced when the HERV-H Env peptide is mixed with another tumor antigen peptide and used as a cancer vaccine in one example of the present invention.

FIG. 7 presents a graph showing the results obtained by measuring the ratios (%) of tumor cells killed by the HERV-H Env-specific CTL induced from HLA-A24 positive CTL isolated from peripheral blood of a healthy individual in one example of the present invention. Note that an anti-HLA antibody was added when the HERV-H Env-specific CTL was induced.

FIG. 8 presents the results of flow cytometric analysis showing the growth of CD8+ cells in pancreas and peripheral blood of immunodeficiency mice after the HERV-H Env-specific CD8+ CTL, which had been induced from HLA-A24 positive monocytes isolated from peripheral blood of a healthy individual with the HERV-H Env peptide, HLA-A24 positive monocytes isolated from peripheral blood of a healthy individual and HERV-H Env peptide were co-administered to the mice in one example of the present invention.

FIG. 9 shows changes in expression levels of the genes which control epithelium-mesenchymal transition (A) and the numbers of membrane-invading cells (B) in the human colon tumor cell line COLO320 expressing endogenous HERV-H Env and Snail, in the case that the expression of HERV-H env gene and Snail gene was inhibited, in one example of the present invention.

FIG. 10 shows changes in expression levels of the genes which control epithelium-mesenchymal transition (A) and the numbers of membrane-invading cells (B) in a human colon tumor cell line SW837, which expresses endogenous HERV-H Env, in the case that the expression of HERV-H env gene was inhibited, in one example of the present invention.

FIG. 11 shows changes in expression levels of the genes which control epithelium-mesenchymal transition (A) and the numbers of membrane-invading cells (B) in a human pancreatic tumor cell line MIAPaca expressing endogenous HERV-H Env and Snail, in the case that the expression of HERV-H env gene and Snail gene was inhibited, in one example of the present invention.

DESCRIPTION OF EMBODIMENTS

Figure 1:
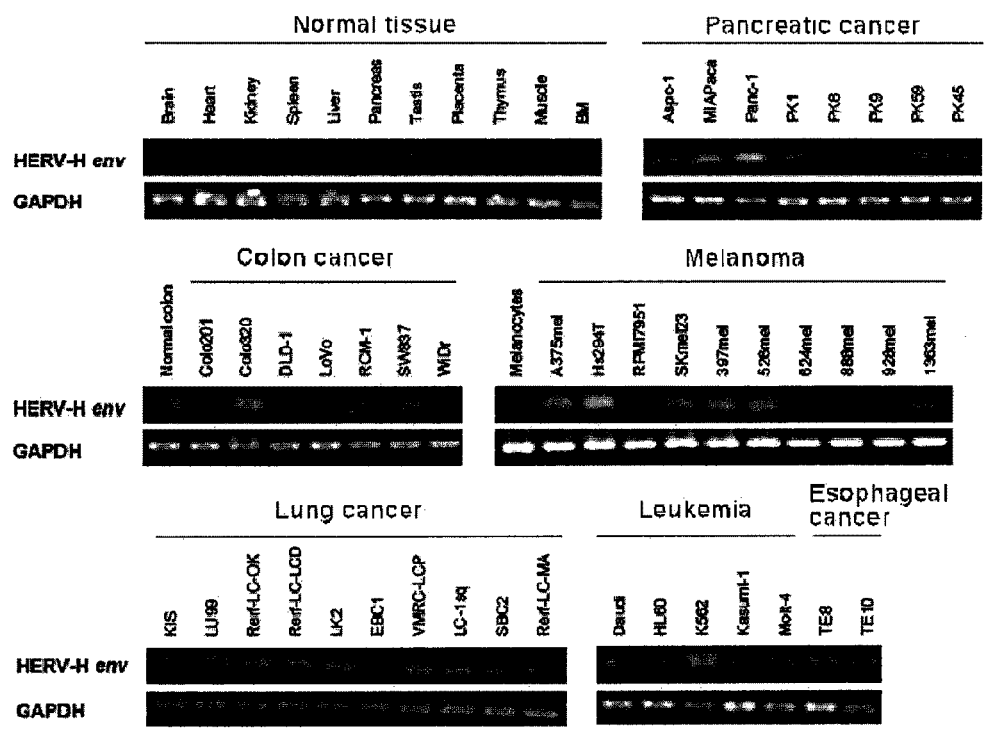
[FIG. 1]
Figure 1:
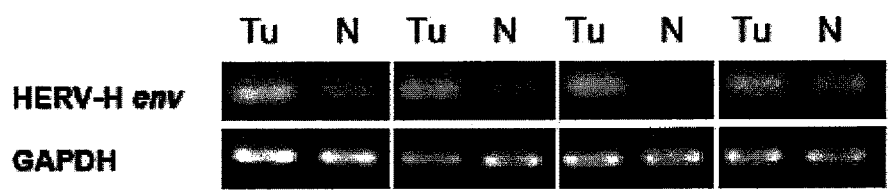

Embodiments of the present invention are hereinafter described in detail by giving Examples. Unless otherwise explained in the embodiments or examples, methods having been described in standard sets of protocols such as J. Sambrook, E. F. Fritsch & T. Maniatis (Ed.), Molecular cloning, a laboratory manual (3rd edition), Cold Spring Harbor Press, Cold Spring Harbor, N.Y. (2001); F. M. Ausubel, R. Brent, R. E. Kingston, D. D. Moore, J. G. Seidman, J. A. Smith, K. Struhl (Ed.), and Current Protocols in Molecular Biology, John Wiley & Sons Ltd., or their modified or altered methods are employed. Commercially available reagent kits and measuring instruments are utilized according to attached instructions unless otherwise indicated.

The object, features, and advantages of the present invention as well as the ideas thereof will be apparent to those skilled in the art from the descriptions given herein, and the present invention can be easily reproduced by those skilled in the art based on the descriptions given herein. It is to be understood that the embodiments and specific examples of the invention described hereinbelow are to be taken as preferred examples of the present invention. These descriptions are presented for illustrative and explanatory purposes only and are not intended to restrict the invention to these embodiments or examples. It is further apparent to those skilled in the art that various alterations and modifications may be made based on the descriptions given herein within the intent and scope of the present invention disclosed herein.

Method for Diagnosing Tumors

The HERV-H env gene is barely detected in normal tissues, and only a weak expression is observed in a few tissues. However, its expression is detectable in variety of carcinomas and tumor cell lines among human cell lines. In fact, HERV-H Env is expressing at high ratio among tumor tissues of clinical patients. Therefore, when the expression of the HERV-H env gene is examined in a tissue or cell sample collected by biopsy etc. and a strong expression of HERV-H env gene is detected, it can be diagnosed as being tumor.

The type of tumor to be diagnosed is not particularly limited, and may be any of solid tumors and blood tumors, including neuroma, kidney cancer, liver cancer, pancreatic cancer, sarcoma, colon cancer, melanoma, lung cancer, esophageal cancer, uterine cancer, testicular cancer, ovarian cancer, leukemia, lymphoma and myeloma. Preferred are the tumors derived from tissues where the expression is not normally detected, such as brain tumor, neuroma, kidney cancer, thymoma, splenic tumor, liver cancer, osteosarcoma, lymphoma and myeloma. Even for tumors derived from tissues where the expression is normally detectable, the diagnosis of the tumor is still possible by comparing the intensity of the expression with the normal tissue and determining whether the expression is enhanced.

The method for the diagnosis is not particularly limited, as long as the expression of the HERV-H env gene can be detected, and may include detection of protein or detection of RNA. In view of simplicity, preferred methods are those using an antibody (such as ELISA), those using PCR (such as RT-PCR) or the like. Thus, a diagnosing kit for enabling easy and simple detection can be provided, which contains a diagnosing agent such as an anti-HERV-H Env antibody capable of detecting the HERV-H Env protein or a PCR primer pair capable of detecting the HERV-H env gene expression. The kit may further include reagents and plates for the ELISA, reagents for the PCR, or the like, in addition to the antibody or the primer pair.

Pharmaceutical Composition and Antitumor Agent, and Method for Treating Tumors Using the Same As explained above, the overexpression of Snail in a tumor is considered to enhance the expression of EMT-associated genes (for example, E-cadherin), facilitating metastasis and invasion of the tumor cells and making the tumor malignant. In Snail-overexpressing tumors, in which the expression of the HERV-H env gene is also enhanced, the enhancement of expression of the downstream genes due to the overexpression of Snail is suppressed when function of the HERV-H Env protein is inhibited. This indicates that the snail gene is located most upstream in a cascade of gene expression control, followed by HERV-H env gene downstream of the snail gene, and the EMT-associated genes further downstream.

When the function of HERV-H Env is inhibited in a Snail-overexpressing tumor, the function of EMT-associated genes is inhibited, thereby enabling suppression of metastasis and/or growth rate of the tumor. In fact, when the function of HERV-H Env is inhibited in a Snail-overexpressing tumor, the number of infiltrating cells decreases and their growth is suppressed. This indicates that a pharmaceutical composition containing a function-inhibiting substance that inhibits the function of HERV-H Env protein can be used as an antitumor agent.

The function-inhibiting substance for suppressing the function of the HERV-H Env protein is not particularly limited, and may be, for example, an anti-HERV-H Env antibody, an siRNA or an antisense RNA. As the mechanism of the inhibition, the expression of HERV-H env gene may be inhibited at the transcription level or at the translation level and the function of HERV-H Env protein may be inhibited.

The tumor to be treated is not particularly limit as long as it is a tumor expressing a Snail protein or a HERV-H Env antigen, and may be any of solid tumors and blood tumors, including neuroma, kidney cancer, liver cancer, pancreatic cancer, sarcoma, colon cancer, melanoma, lung cancer, esophageal cancer, uterine cancer, testicular cancer, ovarian cancer, leukemia, lymphoma and myeloma. Preferably, the tumor is pancreatic cancer, colon cancer, melanoma, lung cancer, leukemia or esophageal cancer, and more preferably colon cancer or pancreatic cancer.

The method to use the antitumor agent may be appropriately chosen, and preferably includes systemic administration to the patient or direct administration to the site of or a vicinity of the tumor.

Cancer Vaccine and Method for Treating and Preventing Tumor Using the Vaccine

If a peptide having any of SEQ ID NOs: 3 to 5, which are parts of the amino acid sequence of the HERV-H Env protein, is added to a dendritic cell that is an antigen-presenting cell, the peptide will be bound with a HLA class I molecule and will be presented on the cell surface and recognized by cytotoxic T-cells, thereby enabling induction of the T cells into HERV-H Env-specific cytotoxic T-cells. The cytotoxic T-cells established by the stimulation with the peptide can efficiently recognize the tumor cells expressing HERV-H Env protein. Therefore, the one or more peptide(s) selected from SEQ ID NOs: 3 to 5, the antigen-presenting cells presenting the selected peptide(s) on the cell surface, and the cytotoxic T-cells induced with the antigen-presenting cell and recognizing tumor cells expressing HERV-H Env antigen, can be used as cancer vaccines for treating and/or preventing tumors.

To date, methods for administering to a tumor patient the tumor specific-tumor antigen, the tumor antigen-presenting cell or the tumor antigen-responsive cytotoxic T-cell have been developed as a cancer vaccine. Since the partial peptide of HERV-H Env is used in the present invention, the tumor to be treated and/or prevented is not particularly limited as long as it is a tumor expressing HERV-H Env, and may be any of solid tumors and blood tumors, including neuroma, kidney cancer, liver cancer, pancreatic cancer, sarcoma, colon cancer, melanoma, lung cancer, esophageal cancer, uterine cancer, testicular cancer, ovarian cancer, leukemia, lymphoma and myeloma. The main target to be treated is the human patients having such a tumor, but non-human vertebrates having a tumor may be treated as well.

Method for Using Cancer Vaccine

Cancer vaccines according to the present invention may contain a peptide having any of SEQ ID NOs: 3 to 5. In this embodiment, the cancer vaccines are administered to a patient having the tumor to be treated. Preferably, the HLA class I type of the patient is determined in advance. The peptide having any of SEQ ID NOs: 3 to 5 is administered if the HLA class I type of the patient is A24 or A02. The peptide to be administered may be of one type or more than one types. The site to be administered is not particularly limited; e.g. intradermally, subcutaneously, intravenously or peritoneally. The peptide may be administered together with an adjuvant or the like to improve immunity-inducing ability. The peptide to be administered may be modified in order to reduce in vivo degradation. Furthermore, the vaccine may be administered as a gene vaccine that include for example an expression vector including a coding gene for the peptide instead of the peptide itself Further, the cancer vaccine may include an antigen-presenting cell presenting a peptide having any of SEQ ID NOs: 3 to 5. In this embodiment, the peptide presented on the cell surface may be the peptide having any of SEQ ID NOs: 3 to 5, which may be further modified by carbohydrate, phosphate or the like. The peptide can be chemically synthesized. Alternatively, the peptide can be prepared by expression of a vector containing a gene encoding the peptide. As for the antigen-presenting cells, not only dendritic cells, but also macrophages, B-cells, and tumor cells (pseudo antigen-presenting cells) having been forcibly expressed a T-cell stimulation factor etc. such as B7 and 4-1 BBL by gene transfer etc., can be considered to be usable, but the dendritic cells are preferable in view of their high antigen-presenting ability. An exemplary method for isolating dendritic cells is hereinafter described.

First, monocytes are isolated from peripheral blood of a vertebrate. The monocytes are isolated preferably from the individual to be treated, but may be isolated from a different individual. The monocytes are is preferably CD14 positive or CD11c positive. The isolated monocytes are induced to differentiate into immature dendritic cells by culturing in the presence of GM-CSF and IL-4 for about 7 days. The induced dendritic cells highly express MHC molecules, which are antigen-presenting molecules. The HLA class I type of the immature dendritic cells is examined and if the type is A24 or A02, the peptide having any of SEQ ID NOs: 3 to 5 as listed below is added to the cells.

```
HERV-H#1:
SYLHHTINL           (SEQ ID NO: 3)

HERV-H#2:
FYSLLLYSL           (SEQ ID NO: 4)

HERV-H#3:
NYAEPPWPL           (SEQ ID NO: 5)
```

An extract or a lysate of cells induced to express the peptide, or a purified peptide from such cells may be added to the dendritic cells instead of the chemically synthesized peptide. The antigen-presenting dendritic cells thus obtained are administered to an individual having tumor. The site to be administered is not particularly limited; e.g. intradermally, subcutaneously, intravenously and intralymphatically. A direct administration into the tumor tissue or a lymph node is preferable in view of the fact that physiological antitumor immunoreactions including the antigen presentation by the dendritic cells take place in the tumor tissue and in vicinity of the tumor such as regional lymph nodes.

Further, cancer vaccines according to the present invention may include a T-cell established by the stimulation with an antigen-presenting cell presenting a peptide having any of SEQ ID NOs: 3 to 5. In this embodiment, the T-cell is co-cultured with the antigen-presenting cell presenting the peptide having any of SEQ ID NOs: 3 to 5 so that the T-cell is stimulated with the antigen-presenting cell. The T-cell thus established may be administered to an individual is having tumor. The T-cell to be used herein is preferably a cytotoxic T-cell, but also may be a helper T-cell or the like. The site to be administered is not particularly limited; e.g. intradermally, subcutaneously, intravenously or intratumorally. For the cytotoxic T-cell, the intratumoral administration is preferable because it allows the cytotoxic T-cell to directly attack the antigen-expressing cell.

Any of the abovementioned cancer vaccines may be administered together with another cancer vaccine. In particular, in an embodiment where any of the peptides having SEQ ID NOs: 3 to 5 are used as the cancer vaccine according to the present invention, the peptide can exert a synergistic effect when it is co-administered with another tumor-antigen peptide capable of acting as a cancer vaccine, because they are viral antigenic peptides and can also serve as an adjuvant to enhance the antigenicity of the co-administered peptide.

EXAMPLES

Embodiments of the present invention are hereinafter described in detail by giving examples. These examples are presented only for the purpose of explaining the present invention, and are not intended to restrict the scope of the present invention.

Example 1

Expression of HERV-H env Gene in Human Normal Tissues and Tumor Cells

This example shows that the endogenous retrovirus HERV-H env gene is hardly expressed in human normal tissue but strongly expressed in tumor cell lines and in tumor tissues.
Method for Analyzing Gene Expression by RT-PCR RNAs were extracted from human normal tissues, various human tumor cell lines and human colon cancer (see FIG. 1) using RNeasy Kit (Qiagen Inc.) and were reverse-transcribed by AMV to obtain cDNAs. By using the primers as listed below, the cDNAs were amplified in iCycler (BioRad Inc.) and analyzed on electrophoresis to detect expression of the genes.

The upper image in each of the panels in FIG. 1 shows the expression of the HERV-H env gene, and the lower image shows the expression of the GAPDH gene as a control for the expression level.

```
Primers for HERV-H env:
Forward
5'-GGATCCTCTACCTACATGTGTC-3'       (SEQ ID NO: 6)

Reverse
5'-TCAAGGGAATTAGTGGAATAAC-3'       (SEQ ID NO: 7)

Primers for GAPDH:
Forward
5'-GTCAACGGATTTGGTCGTATT-3'        (SEQ ID NO: 8)

Reverse
5'-ATCACTGCCACCCAGAAGACT-3'        (SEQ ID NO: 9)
```

As shown in FIG. 1A, weak expression of the HERV-H env gene was detected in heart, spleen, pancreas, testis and placenta among the human normal tissues tested, whereas no expression was detected in brain, kidney, liver, thymus, skeletal muscle and bone marrow (BM). Among the human tumor cell lines tested, strong expression of the HERV-H env gene was detected in various types of tumors (pancreatic cancer, colon cancer, melanoma, lung cancer, leukemia and esophageal cancer) and in tumor cell lines derived them. As shown in FIG. 1B, the colon cancer tissue (Tu) exhibited a higher level of expression than the normal tissue (N).

Thus, the expression of the HERV-H env gene can be utilized for diagnosing tumors. The method for treating tumors by targeting HERV-H Env as the tumor antigen is also applicable to patients with a wide variety of tumors with little side effect on various tissues.

Example 2

Function of HERV-H Env Expressed in Tumor Cells and Inhibition Thereof

This example shows that HERV-H Env is involved in invasion of tumor cells and that the invasion can be suppressed by inhibiting the expression of the HERV-H env gene.
(1) Forced Expression of Snail Gene in Panc-1 Cells First, snail cDNA (CDS 71-865, 795 bp) was amplified by PCR using the Panc-1 cells that had been stimulated with TGF-beta known as an EMT-inducing agent, and was inserted into the EcoR I-Xho I restriction sites of pcDNA3.1 (+) plasmid vector (Invitrogen Inc.) having a G418 resistance gene. The vector was introduced into the tumor cell lines by electroporation. The cells were cultured for 2 weeks and then drug-resistant cells were selected with G418 (2 mg/mL) and cloned.

Figure 2:
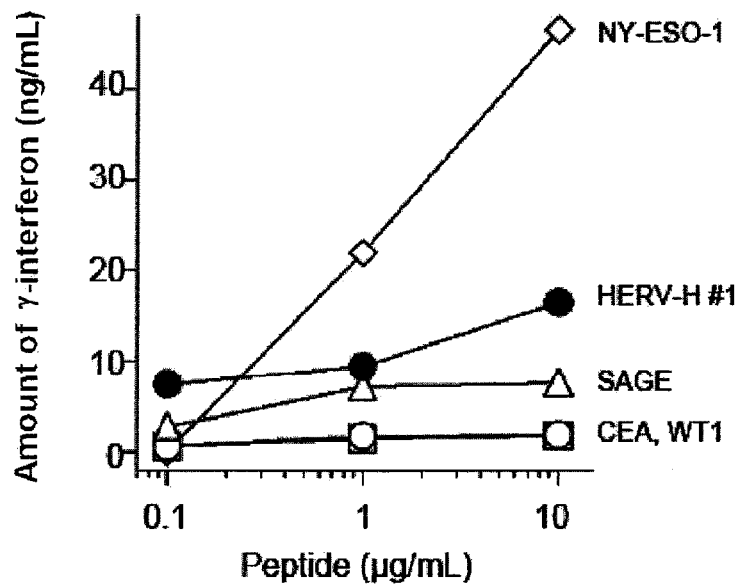
[FIG. 2]
Figures 3, 5:
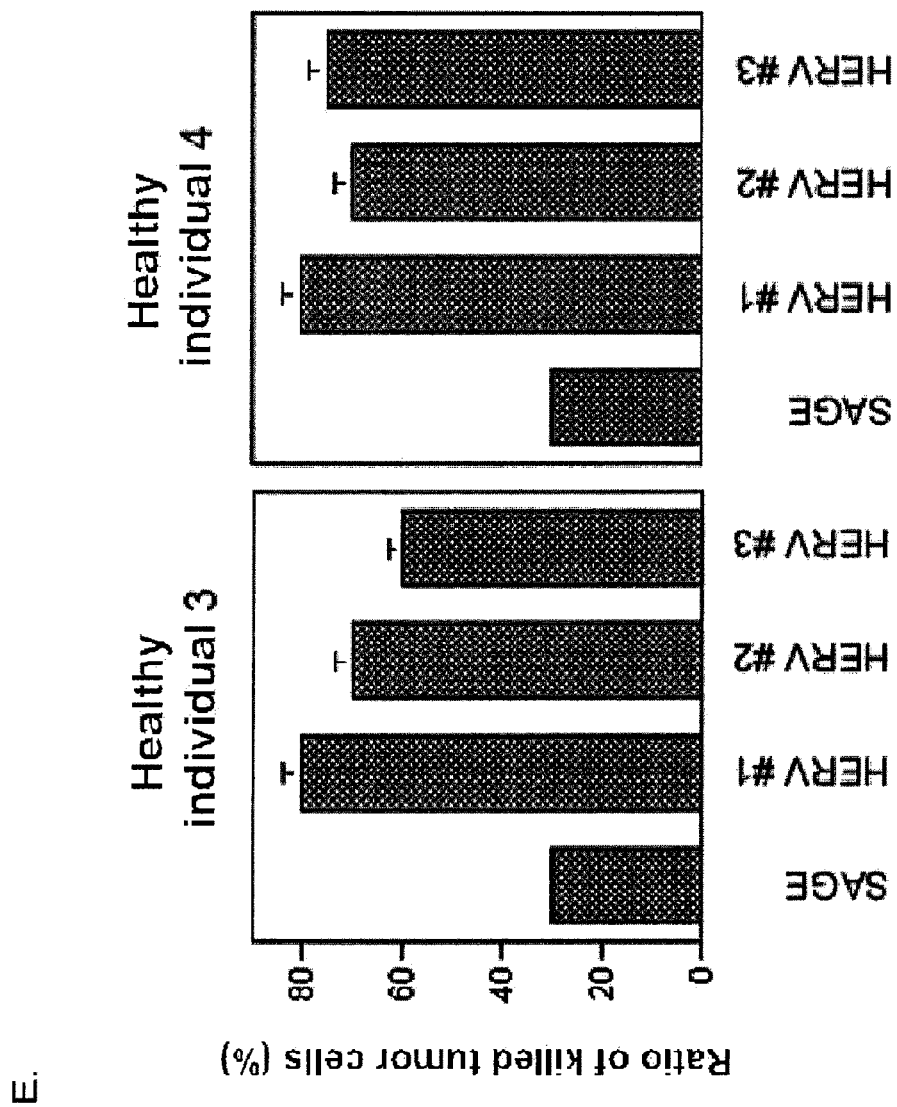

FIG. 2 shows a table that summarizes phenotypes of snail gene-introduced cell lines.

While the endogenous expression of Snail protein could be observed in the parent Panc-1 cells, the expression levels of Snail protein were further enhanced in clones D6, D10, F3 and F5 into which the expression vector of the snail gene was introduced. As a result, in all of the clones, the cell morphology was altered from a round shape to a flattened spindle/spreading shape, the cell proliferation rate was reduced both in vitro and in vivo, the protein level and cell adhesion capability of E-cadherin were reduced, and the migration capability and invasion capability of the cells were enhanced. Particularly in Clone F3, a significant effect on the epithelium-mesenchymal transition (EMT) was observed, and thus Clone F3 was further used in the following Examples.

(2) Effect of Suppression of HERV-H env Gene Expression in Clone F3

In this example, the expression of HERV-H env gene was suppressed in Clone F3 and cell invasion capability and growth rate were measured.

First, $5\times10^4$ of F3 cells, as well as F3 cells (#1 to #4, Invitrogen Inc.) that had been cultured for 2 to 3 days after transfected with each of the 4 kinds of HERV-H env gene specific-siRNAs (shown below) by PEI complex method (Polyplus Inc.), were counted. The numbers of cells as plotted in the graph of FIG. 3A were taken as a standard of the growth rates.

Method for Measuring Cell Invasion Capability

Then, the recovered cells were placed on the upper surface of the Invasion Chamber (pore size 8 μm, BD Bioscience Inc.) whose membrane was coated with matrigel, and cultured for 4 hours (37° C., 5% $CO_2$). After cells remaining on the upper surface of the membrane were removed completely, the cells invaded into the lower surface of the membrane were fixed and stained with Crystal Violet solution and counted under a microscope to evaluate the cell invasion capability.

For control experiments, F3 cells (Control) transfected with a control oligonucleotide from Invitrogen, F3 cells (siRNA-snail) transfected with snail gene specific-siRNA (SiRNA-snail #1) (shown below) and a Panc-1 cell line (Parent) were used.

```
siRNA-HERVH#1:
Sense:
CCAAUCUUAUGCCACCCUUdTdT      (SEQ ID NO: 10)

Antisense:
AAGGGUGGCAUAAGAUUGGdTdT      (SEQ ID NO: 11)

siRNA-HERVH#2:
Sense:
CCAAUUCUUAGUCCUUUAAdTdT      (SEQ ID NO: 12)

Antisense:
UUAAAGGACUAAGAAUUGGdTdT      (SEQ ID NO: 13)

siRNA-HERVH#3:
Sense:
CCAGGCCAUCACCGAUCAUdTdT      (SEQ ID NO: 14)

Antisense:
AUGAUCGGUGAUGGCCUGGdTdT      (SEQ ID NO: 15)
```

```
siRNA-HERVH#4:
Sense:
GGAGGACUCUGUAUAUUCUdTdT      (SEQ ID NO: 16)

Antisense:
AGAAUAUACAGAGUCCUCCdTdT      (SEQ ID NO: 17)

siRNA-snail#1:
Sense:
GCGAGCUGCAGGACUCUAAdTdT      (SEQ ID NO: 18)

Antisense:
UUAGAGUCCUGCAGCUCGCdTdT      (SEQ ID NO: 19)

Control Oligonucleotide:
Sense:
GGAUCAGUCUAUUAGGUCUdTdT      (SEQ ID NO: 20)

Antisense:
AGACCUAAUAGACUGAUCCdTdT      (SEQ ID NO: 21)
```

Figure 3:
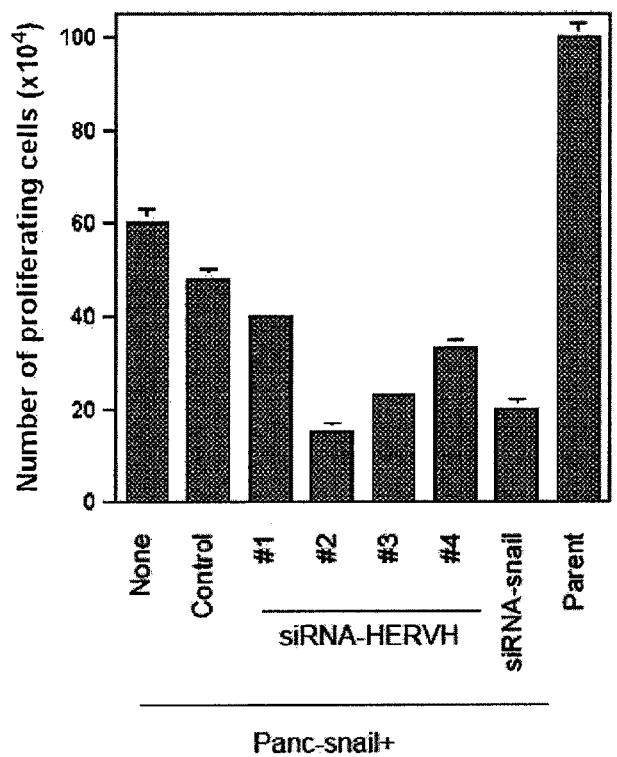
[FIG. 3]
Figure 3:
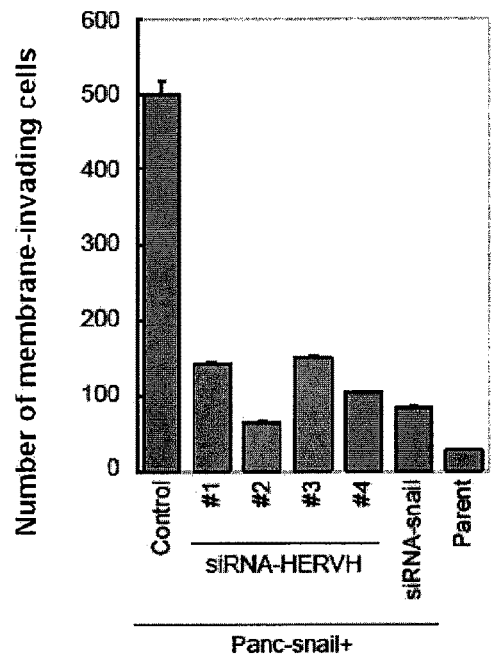

The cell growth were strongly suppressed in the HERV-H-inhibited F3 cells (shown as #1 to #4 in the figure) like the cells transfected with the Snail-specific siRNA (shown as "siRNA-snail" in the figure) in contrast to the untreated cells (shown as "None" in the figure) and those transfected with the control siRNA (shown as "Control" in the figure), as shown in FIG. 3A.

While the F3 cell line has an enhanced cell invasion capability in contrast to the parent Panc-1 cell line (shown as "Parent" in the figure), the cell invasion capability of the F3 cell line was significantly reduced when the F3 cells were transfected with the HERV-H env gene specific-siRNA, similarly to the cells transfected with the Snail-specific siRNA, as shown in FIG. 3B.

Since the HERV-H Env protein functions downstream of the snail protein, the inhibition of the HERV-H Env protein function can suppress the effect of forced expression of the snail gene on the cell functions such as the growth rate and the cell invasion capability. In other words, the growth rate and cell invasion capability of tumor cells overexpressing the snail gene can be reduced by inhibiting the function of HERV-H Env. Therefore, an inhibitor capable of inhibiting the function of HERV-H Env is useful as an antitumor agent (i.e. a growth suppression agent and/or an anti-metastatic agent).

Example 3

Induction of HERV-H Env Specific-CTL using Genetically Modified Mouse Expressing HLA-A24

In this example, genetically modified mice expressing HLA-A24 (A24-Tg) (purchased from SLC Inc.; see International J. Tumor 100: 5565-5570, 2002) were immunized with HLA-A24-restricted HERV-H Env peptide to show that HERV-H Env has immunogenicity, i.e. a CTL specific for HERV-H Env can be induced.

First, dendritic cell precursors were isolated from bone marrow cells of A24-Tg mice using LineagePanel Streptavidin Plus Magnetic Particles-DM (BD Biosciences Inc.) and cultured for 6 days in the presence of GM-CSF (10 ng/mL, Peprotech Inc.) to induce their differentiation. The dendritic cells thus obtained were cultured for 6 hours in the presence of each of the peptides having the sequences shown below (10 μg/mL, synthesized by Invitrogen Inc.), and then injected subcutaneously to genetically modified mice expressing HLA-A24 at $5\times10^6$ cells per mouse for immunization. In addition, SAGE which has been identified as a testicular tumor antigen and for which a HLA-A24-restricted peptide has been established, was used for a positive control experiment (Cancer Research 60:3848-3855, 2000), and dendritic cells not stimulated by a peptide were used as the negative control.

```
HERV-H#1:
SYLHHTINL        (SEQ ID NO: 3)

HERV-H#2:
FYSLLLYSL        (SEQ ID NO: 4)

HERV-H#3:
NYAEPPWPL        (SEQ ID NO: 5)

SAGE:
LYKPDSNEF        (SEQ ID NO: 22)
```

Spleen cells were collected from the mice one week after the immunization with each of the peptides, and were cultured under the stimulation by 10 μg/mL of the same peptide as used for immunization for 6 days, from which CD8+ cells were isolated by the MACS method using antibody-coupled magnetic beads from Miltenyi Inc . In order to produce cytokine at a higher level, the CD8+ cells ($1\times10^6$) were further stimulated for 24 hours by 0.08 to 10 μg/mL of the same peptide in the presence of APC ($1\times10^7$ cells) that was obtained by collecting the spleen cells freshly from a HLA-A24 expressing-genetically modified mouse and then inactivating the cells with mitomycin C. Amounts of gamma interferon contained in the culture supernatants were measured by Cytometric Bead Array kit for mouse (BD Biosciences Inc.).

Figure 4:
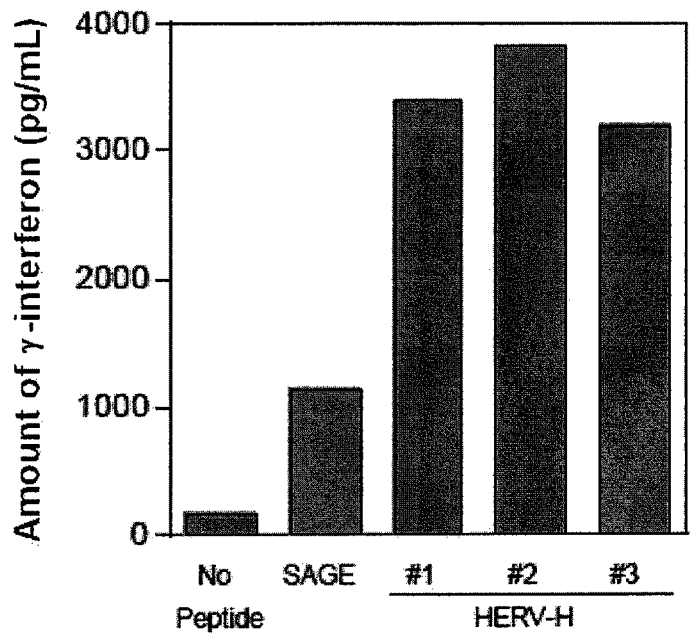
[FIG. 4]
Figure 4:
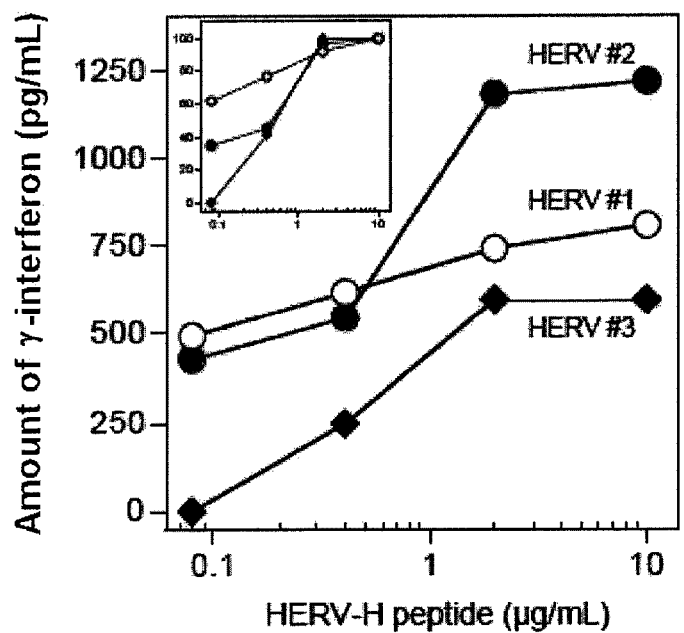

FIG. 4A shows the amounts of gamma interferon produced after the CD8+ cells were stimulated by 10 μg/mL each of the peptides. All of the three HERV-H Env peptides tested were able to induce the CD8+ cells highly producing gamma interferon in the immunized A24-Tg mice in response to HERV-H Env antigen, and the activity of the induction was stronger than the SAGE peptide.

FIG. 4B shows the amounts of gamma interferon produced after the CD8+ cells were stimulated by each of the peptides at concentrations of 0.08 to 10 μg/mL. In the upper-left corner, the values of the amount of gamma interferon produced after the stimulation at various peptide concentrations were plotted; it should be noted that the values had been normalized by the amount of gamma interferon produced after stimulation by the peptide at 10 μg/mL as 100%. By comparing among the HERV-H Env peptides, HERV-H#2 exhibited the highest activity, but the activities of HERV-H#2 and HERV-H#3 were significantly reduced at lower concentrations below 2 μg/mL, whereas the activity of HERV-H#1 was maintained at lower concentrations. This indicates that the TCR-binding affinity of HERV-H#1 is significantly higher than the other peptides ($P<0.001$, t-test).

Example 4

Induction of HERV-H Env-Specific CTL Using Monocytes from Peripheral Blood of Healthy Individual This example shows that the HERV-H Env peptide including any of SEQ ID NOs: 3 to 5 can induce CTL specific for HERV-H Env not only in the genetically modified mice expressing HLA but also in human.

First, blood was collected from two healthy individuals positive for HLA-A24, to which 1/10 volume of 4% sodium citrate was added, and was overlaid on Ficoll-Paque (Amersham Inc.) and centrifuged (1500 rpm, 20 min, room temperature). The fraction of monocytes (PBMC) separated in the interface was cultured for 6 days under the stimulation with 10 μg/mL of each peptide, from which CD8+ cells were isolated by the MACS method using antibody-coupled magnetic beads (Miltenyi Inc). In order to estimate cytotoxic activity of the isolated CD8+ cells, they were cocultured with human colon cancer cell line COLO320 (HLA-A24$^+$ SAGE$^+$ HERV-H $^+$ Env$^+$) as the target cell at a mixing ratio of [CD8+ cell:COLO320 tumor cell=50:1] for 6 hours. The killed tumor cells were detected using Immunocyto Cytotoxicity Detection Kit (MBL inc.), and tumor-specific toxicity rates were calculated according to the protocol attached to the kit. Results are plotted in the graph of FIG. 5A.

Figures 1, 5:
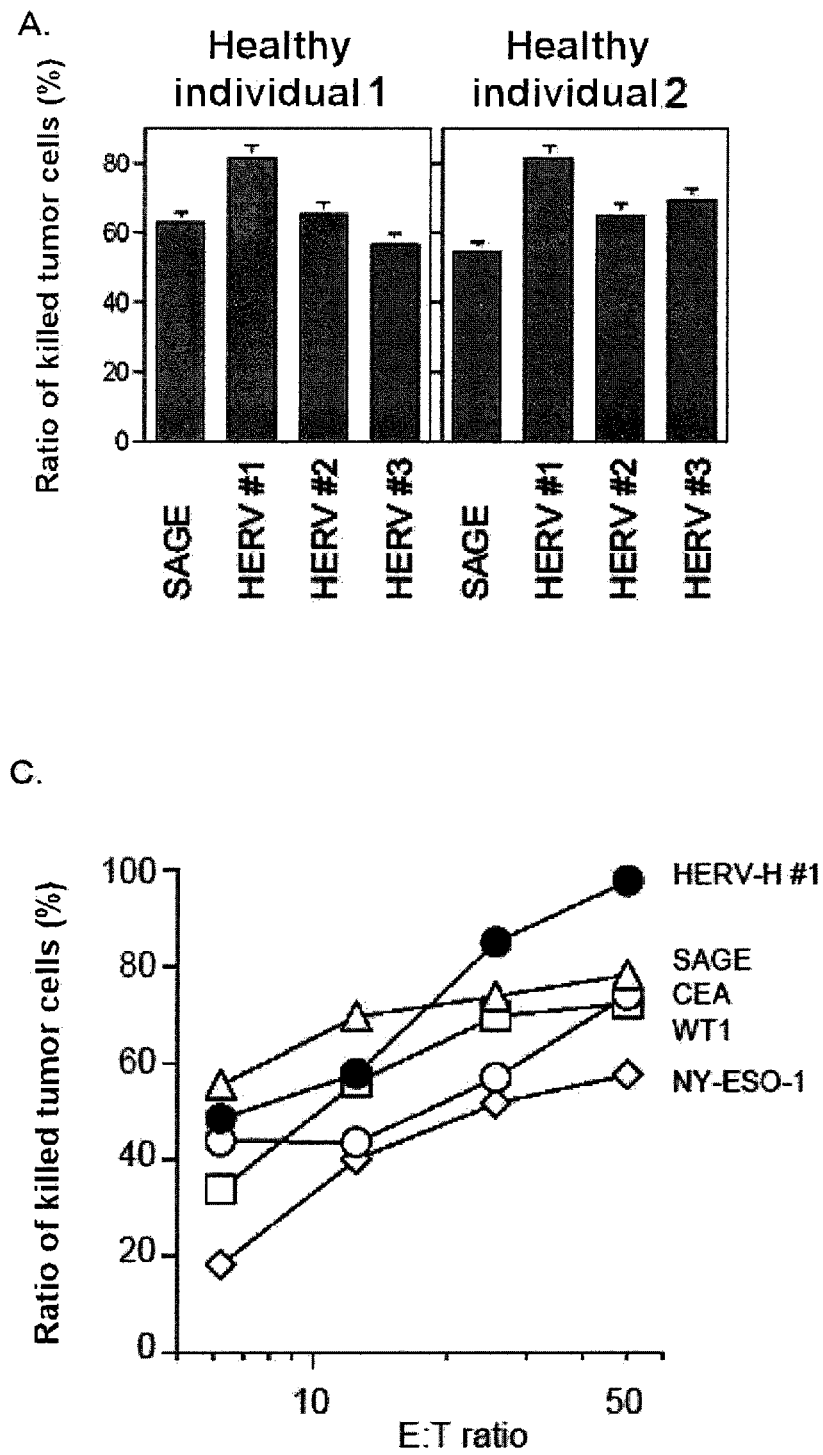
Figure 5:
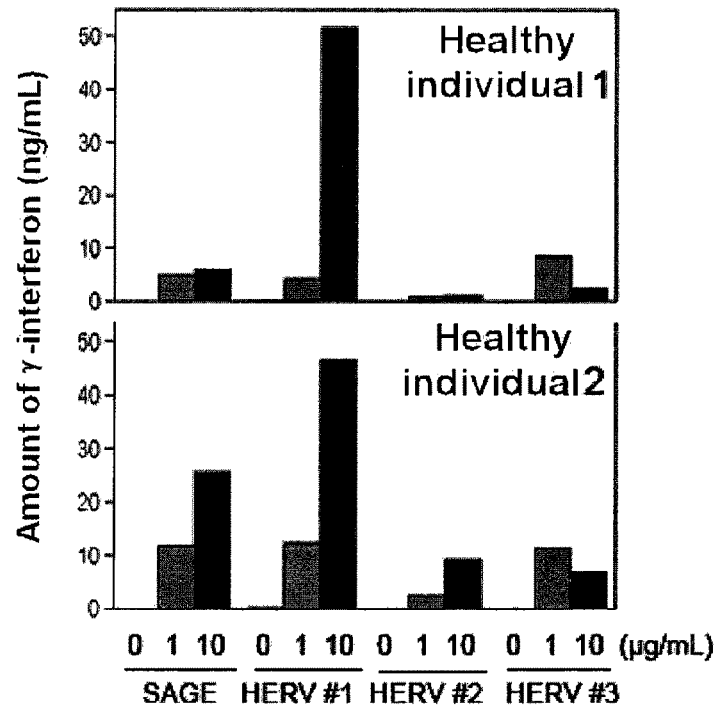

As shown in FIG. 5A, the HERV-H Env peptides were able to induce CD8+ cells sufficiently capable of killing COLO320 tumor cells from the PBMCs derived from both the healthy individuals, at the same level as or higher than the SAGE peptide. The toxicity against tumor cells was the highest in the case of HERV-H#1-induced CTL.

In order to evaluate the gamma interferon production capability, $1\times10^6$ of CD8+ cells were stimulated by 1 or 10 μg/mL of each peptide for 24 hours in the presence of IL-2 (100 U/mL, Peprotech Inc.) and APC ($5\times10^6$ cells) which was obtained by collecting the PBMCs freshly from a healthy individual and then inactivating them with mitomycin C. Amounts of gamma interferon contained in the culture supernatants were measured by Cytometric Bead Array kit for human (BD Biosciences Inc.). Results are plotted in the graph of FIG. 5B.

As shown in FIG. 5B, while little difference was observed between the stimulations at the lower concentration (1 μg/mL) of each peptide, the stimulation of HERV-H#1 at the higher concentration (10 μg/mL) caused significantly higher production than the other peptides.

Further, in the case where PBMCs collected from two healthy individuals positive for HLA-A02 were used in the same method as described above, the stimulation with the HERV-H Env peptides having SEQ ID NOs: 3 to 5 induced CD8+ cells sufficiently capable of killing human pancreatic tumor cell line Panc-1 (HLA-A24$^-$HLA-A02$^+$ SAGE$^+$ HERV-H$^+$ Env$^+$), and the highest toxicity against tumor cells was observed in the case of HERV-H#1-induced CTL, as shown in FIG. 5E.

Thus, all of the HERV-H Env peptides having any of SEQ ID NOs: 3 to 5 were capable of inducing HERV-H Env-specific CTL in the human of both HLA-A24 positive type and HLA-A02 positive type, but the peptide HERV-H#1 having SEQ ID NO: 3 was the most effective in terms of the toxicity against tumor cells and the gamma interferon production capability.

Then, the toxicity against tumor cells and the gamma interferon production capability of the peptide HERV-H#1 having SEQ ID NO: 3 were compared to those of HLA-A24-restricted tumor antigen peptides listed below, are being clinically used in the most advanced peptide vaccine treatments.

```
NY-ESO-1:
LLMWITQCF        (SEQ ID NO: 23)

CEA:
TYACFWSNL        (SEQ ID NO: 24)

WT1:
CMTWNQMNL        (SEQ ID NO: 25)
```

The toxicity against tumor cells was evaluated by setting the ratio of CD8+ cells:COLO320 tumor cells to 6.25:1, 12.5:1, 25:1 or 50:1. The results are plotted in the graph of FIG. 5C. As shown in FIG. 5C, when the ratio of CD8+ cells:COLO320 tumor cells was lower than 25:1, the toxicity was similar to those of SAGE, WT1 etc., but when the E:T ratio was equal to or more than 25:1, the CTL induced by the peptide HERV-H#1 exhibited the highest toxicity.

The gamma interferon production capability was evaluated by stimulating CD8+ cells with 0.1, 1 or 10 µg/mL of each peptide in the presence of IL-2 and APC. The results are plotted in the graph of FIG. 5D. As shown in FIG. 5D, the CTL induced by NY-ESO-1 exhibited the best production at the peptide concentrations equal to or higher than 1 µg/mL, whereas the activity of NY-ESO-1-induced CTL was significantly reduced at the lower peptide concentration (0.1 µg/mL). In contrast, the activity of the CTL induced by HERV-H#1 was the second best after NY-ESO-1 at the concentrations equal to or higher than 1 µg/mL, and was still sufficient to induce gamma interferon production at the lower peptide concentration (0.1 µg/mL).

Thus, the peptide HERV-H#1 having SEQ ID NO: 3 exhibited excellent effects over the conventional peptides being used clinically.

Example 5

Usefulness of HERV-H Env peptide as adjuvant

This example shows that the HERV-H Env peptide can exert a synergistically enhanced immunoreactivity when used as a cancer vaccine mixed with another tumor antigen peptide.

PBMCs were collected from a healthy individual in the same method as Example 4, and CD8+ cells (1×10$^6$) were isolated after stimulation with each of the peptides HERV-H#1, NY-ESO-1, CEA and WT1 (final concentration 10 µg/mL) for 6 days, and further stimulated with each of the peptides HERV-H#1, NY-ESO-1, CEA and WT1 (final concentration 1.0 pg/mL) plus additional HERV-H#1 (final concentration 0.5 µg/mL) in the presence of IL-2 and APC for 24 hours (that is, the HERV-H Env group was stimulated by HERV-H#1 only, and the final concentration in total of peptide(s) in all of the groups was 1.5 µg/mL). Amounts of gamma interferon contained in the culture supernatants were measured by Cytometric Bead Array kit for human, and results are plotted in the graph of FIG. 6. Cells to which only HERV-H#1 was added at a concentration of 0.5 µg/mL were used as a control.

Figure 6:
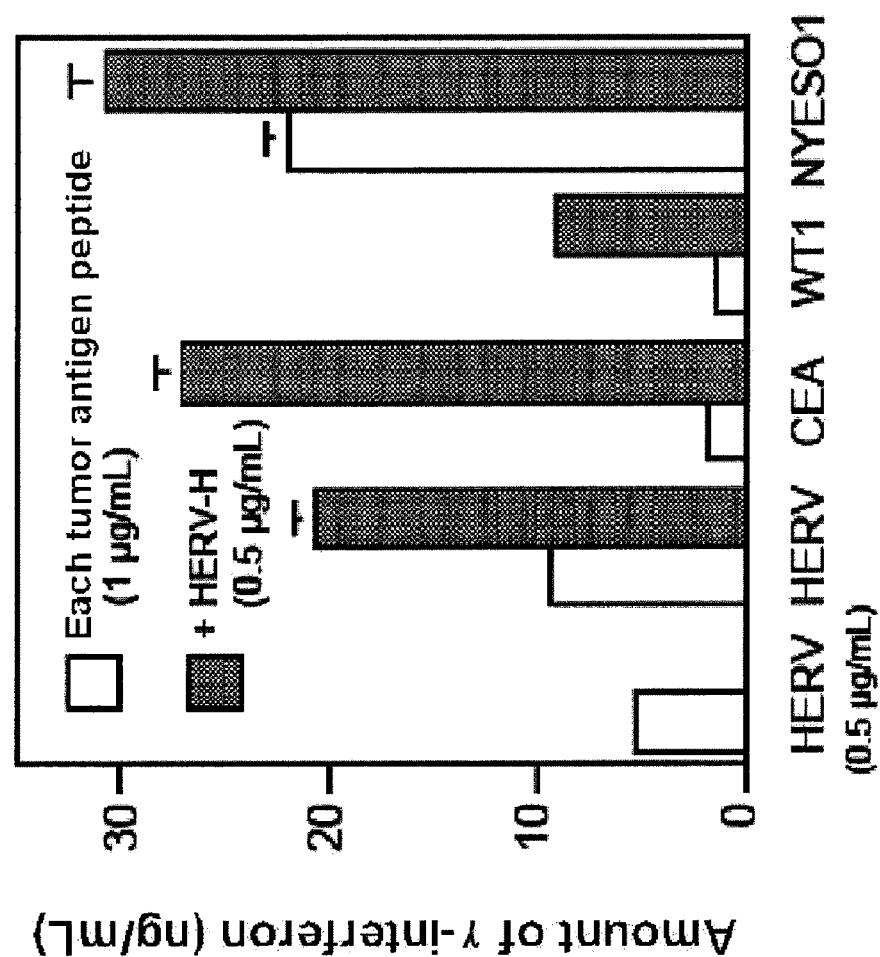
[FIG. 6]

As shown in FIG. 6, in comparison to the cases where each of the peptides alone was used for stimulation, the gamma interferon-producing capability was synergistically enhanced when each of them received the addition of HERV-H Env peptide. This indicates that HERV-H Env peptide is useful as an adjuvant when added to a conventional peptide vaccine treatment.

Example 6

Inhibition of Induction of HERV-H Env-Specific CTL with Anti-HLA Antibody

This example shows that a specific CTL induction with HERV-H Env peptide can be specifically restricted by HLA.

PBMCs collected from a healthy individual in the same method as in Example 4 were cultured with stimulation by HERV-H#1 (final concentration 10 µg/mL) for 6 days in a medium supplemented with an anti-HLA antibody (final concentration 10 µg/mL), from which CD8+ cells were then isolated by the MACS method using antibody-coupled magnetic beads (Miltenyi Inc.). In order to estimate the cytotoxic activity of the isolated CD8+ cells, they were cocultured with human colon tumor cell line COLO320 (HLA-A24$^+$ SAGE$^+$ HERV-H$^+$ Env$^+$) as the target cell at mixing ratios of [CD8+ cell : COLO320 tumor cell=6.25:1, 12.5:1, 25:1 and 50:1] for 6 hours. The killed tumor cells were detected using Immunocyto Cytotoxicity Detection Kit (MBL inc.), and tumor-specific toxicity ratios were calculated by following the protocol attached to the kit. A control group was similarly treated except that the cells were cultured with stimulation in a medium without addition of the anti-HLA antibody.

Figure 7:
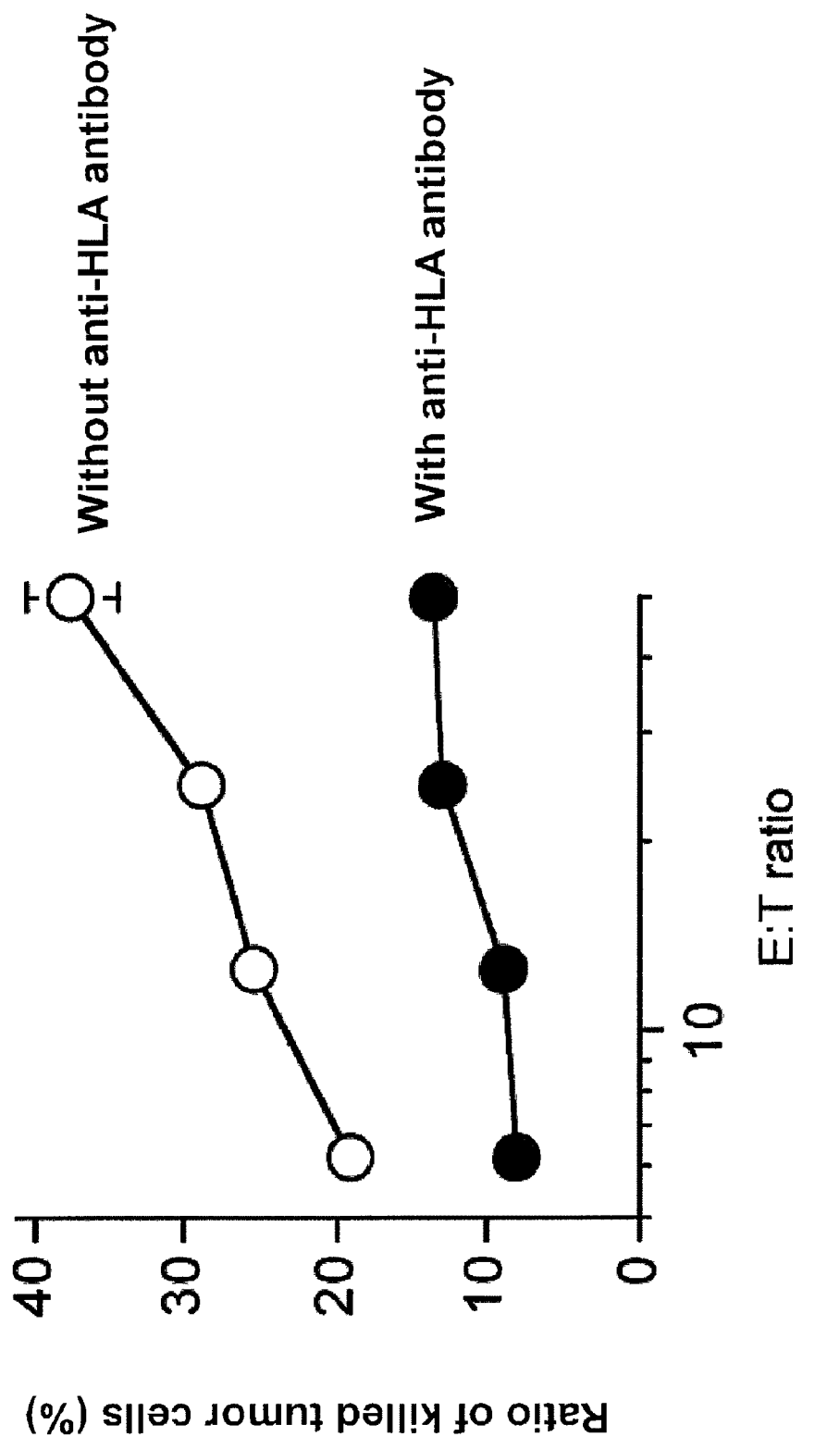
[FIG. 7]

The ratios of killed tumor cells in the group cultured with stimulation in a medium with the anti-HLA antibody were significantly lower than the group without the antibody (control) as shown in FIG. 7.

The fact that the addition of anti-HLA antibody significantly reduced the ratio of killed tumor cells by inhibiting the binding of HERV-H Env antigen peptides with HLA antigens on the PBMCs indicates that most of the CD8+ cells induced by the HERV-H Env peptide are the CD8+positive cytotoxic T-cells which can specifically recognize HERV-H Env antigens presented with HLA on tumor cells and kill the tumor cells.

Example 7

In vivo proliferation of CD8+ Cell by HERV-H Env Peptide

This example shows that CD8+ cells can self-proliferate in the body of an immunodeficiency mouse with stimulation with HERV-H Env peptide.

In the same method as described in Example 4, CD8+ cells were obtained by culturing PBMCs with the stimulation of HERV-H#1 (final concentration 10 µg/mL). The CD8+ cells for a control group were obtained by culturing under the stimulation by NY-ESO-1 peptide (SEQ ID NO: 23) in place of HERV-H#1 at the same concentration. The CD8+ cells thus obtained were fluorescence-labeled by mixing with a fluorescent dye PKH67 (Sigma Corp.) and incubating for 10 min.

The PKH67-labeled CD8+ cells (2×10$^6$ cells), PBMCs (2×10$^7$ cells) collected from the same healthy individual, and a peptide (HERV-H Env or NY-ESO-1 (control groups) at 100 µg per animal) were injected via the tail vein of immunodeficiency mice (the SCID mice, CLEA Japan Inc.). Spleen cells and peripheral blood cells were collected from the mice on 5 days after the administration, and the content of PKH67-labeled CD8+ cells was measured by flow cytometry (BD Inc.). Mice treated similarly except that no peptide was administered were used for a control experiment.

Figure 8:
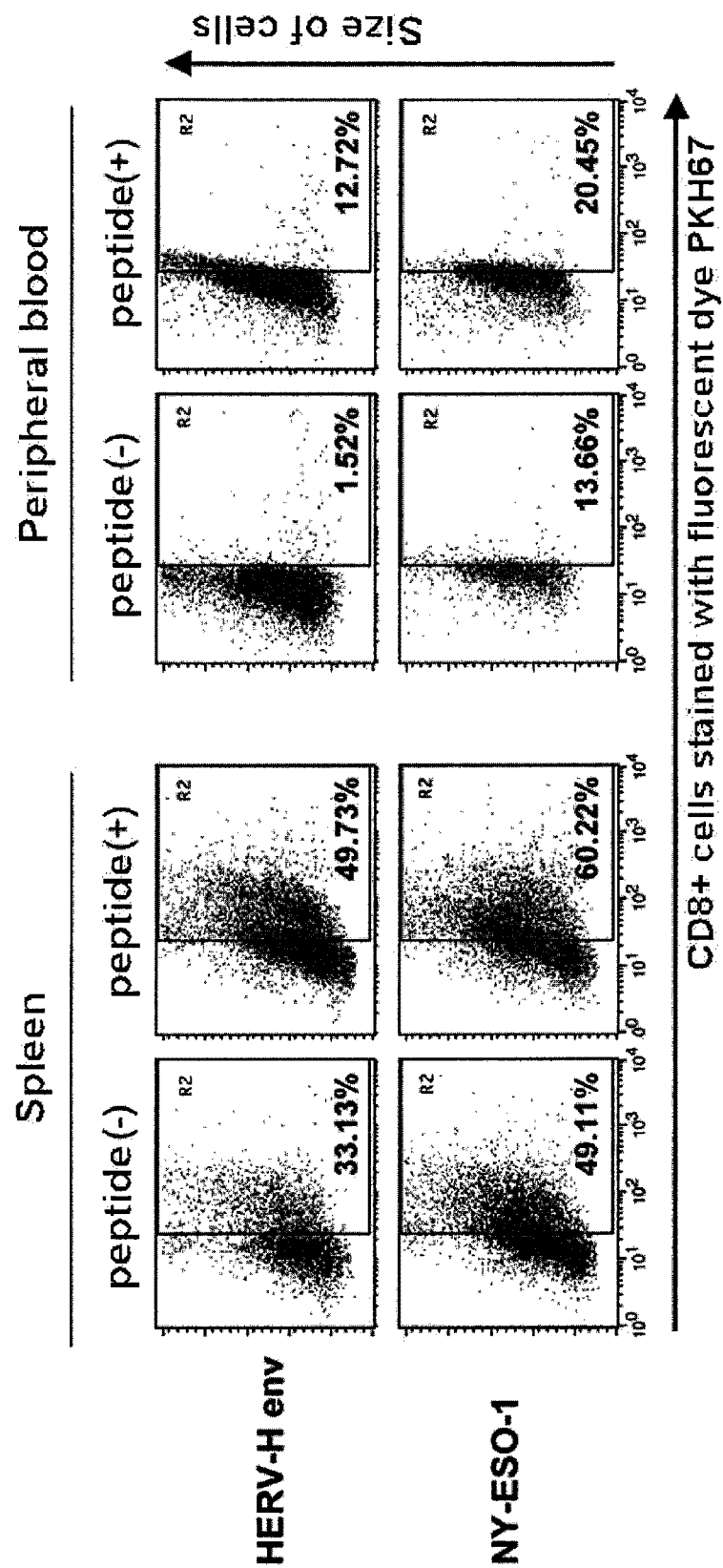
[FIG. 8]

The mouse groups to which either of the HERV-H Env peptide and the NY-ESO-1 peptide was administered exhibited a higher content of CD8+ cells in vivo than the mouse groups without the administration of the peptide, as shown in FIG. 8. This indicates that the growth of CD8+ cells was facilitated by the administration of the peptides. Of the cases where no peptide was administered to the mice, the self-proliferation of the CD8+ cells induced by HERV-H Env peptide was less active than that of the CD8+ cells induced by NY-ESO-1 peptide, and of the cases where the peptides were administered, the proliferation activity of the CD8+ cells induced by HERV-H Env peptide was higher than that of the CD8+ cells induced by NY-ESO-1 peptide. Thus the CD8+ cells induced by the HERV-H Env peptide appears to grow in a manner more antigen-specific than the CD8+ cells induced by the NY-ESO-1 peptide. The same tendency was observed in the spleen and in the peripheral blood.

These results show that the CD8+ cells induced by HERV-H Env peptide can proliferate in vivo, and this proliferation has high antigen specificity for HERV-H Env peptide. Accordingly, HERV-H Env peptide is even more useful for an in vivo vaccine treatment.

Example 8

Function of HERV-H Env and Snail in Tumor Cells Expressing Endogenous HERV-H Env and Snail, and Suppression of the Function This example shows that HERV-H Env and Snail are involved in cell invasion of tumor cells expressing endogenous HERV-H Env and Snail, and that invasion of colon tumor cells can be suppressed by inhibiting expression of HERV-H env gene or Snail gene.

First, cells from the human colon tumor cell line COLO320 were transfected with the siRNAs (SEQ ID NOs: 10 to 19) which specifically inhibit HERV-H env or snail and the control oligonucleotides (SEQ IL) NOs: 20 and 21) (Invitrogen Inc.) by the PEI complex method (Polyplus Inc.), and cultured for 2 to 3 days. It should be noted that COLO320 is a cell line that expresses both of endogenous HERV-H Env and Snail.

RT-PCR was conducted using the primers listed below by following the "Method for Analyzing Gene Expression by RT-PCR" as described in Example 1 and expression of the genes of HERV-H env, Snail, Slug, Twist, E-cadherin, Fibronectin and GAPDH (as an internal standard) were examined.

```
Primers for HERV-H env:
Forward
                                           (SEQ ID NO: 6)
5'-GGATCCTCTACCTACATGTGTC-3'

Reverse
                                           (SEQ ID NO: 7)
5'-TCAAGGGAATTAGTGGAATAAC-3'

Primers for Snail:
Forward
                                           (SEQ ID NO: 26)
5'-CAGATGAGGACAGTGGGAAAGG-3'

Reverse
                                           (SEQ ID NO: 27)
5'-ACTCTTGGTGCTTGTGGAGCAG-3'

Primers for Slug:
Forward
                                           (SEQ ID NO: 28)
5'-AGCGAACTGGACACACATAC-3'

Reverse
                                           (SEQ ID NO: 29)
5'-TCTAGACTGGGCATCGCAG-3'

Primers for Twist:
Forward
                                           (SEQ ID NO: 30)
5'-GCAAGCTTAGAGATGATGCAGGACG-3'

Reverse
                                           (SEQ ID NO: 31)
5'-GACTCGAGGTGGGACGCGGACATGGA-3'
```

```
Primers for E-cadherin:
Forward
                                           (SEQ ID NO: 32)
5'-TTCCTCCCAATACATCTCCCTTCACAGCAG-3'

Reverse
                                           (SEQ ID NO: 33)
5'-CGAAGAAACAGCAAGAGCAGCAGAATCAGA-3'

Primers for Fibronectin:
Forward
                                           (SEQ ID NO: 34)
5'-CCGTGGGCAACTCTGTC-3'

Reverse
                                           (SEQ ID NO: 35)
5'-TGCGGCAGTTGTCACAG-3'

Primers for GAPDH:
Forward
                                           (SEQ ID NO: 8)
5'-GTCAACGGATTTGGTCGTATT-3'

Reverse
                                           (SEQ ID NO: 9)
5'-ATCACTGCCACCCAGAAGACT-3'
```

The human colon tumor cell line COLO320 cultured for 2 to 3 days after the introduction of siRNAs were recovered, and the number of cells whose cell membrane was invading into the lower surface (membrane invading cell number) was counted by following the "Method for Measuring Cellular Invasion Capability" as described in Example 1.

Figure 9:
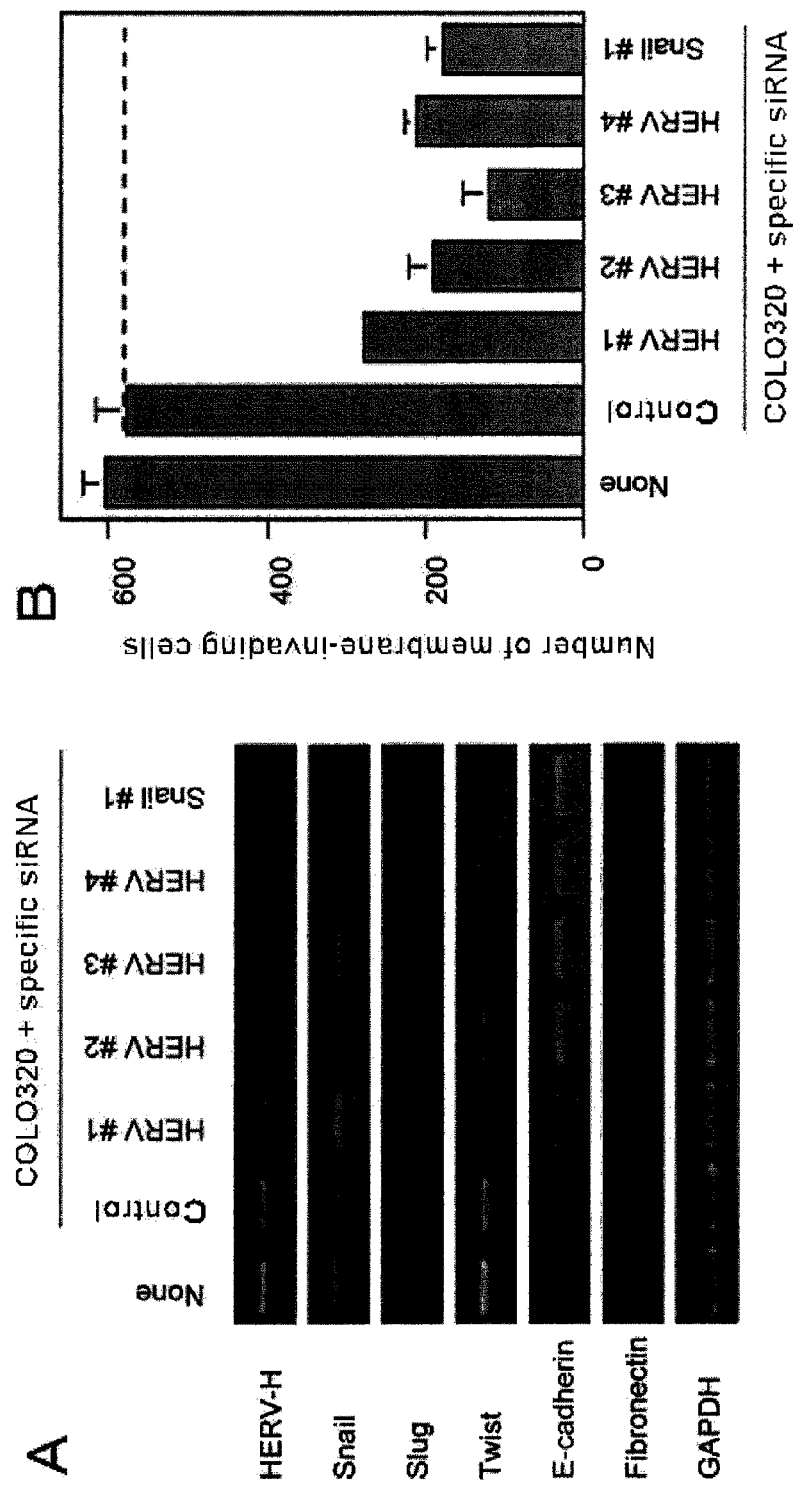
[FIG. 9]

As shown in FIG. 9A, the expression of HERV-H Env was detected in the siRNA non-transfected group (None), confirming that the COLO320 cells were expressing endogenous HERV-H Env. In the cases where the expression of HERV-H env was inhibited by the siRNAs (HERV#1 to 4), the expression levels of the HERV-H env gene decreased, and at the same time, the expression levels of Snail, Slug, Twist and Fibronectin decreased, while the expression level of E-cadherin increased. Since these genes are known to control the epithelium-mesenchymal transition, the results indicate that malignancy of tumors can be reduced by inhibiting the expression of HERV-H Env. Also, the number of membrane invading cells was lowered by the transfection with the siRNAs which inhibit expression of HERV-H Env or Snail as shown in FIG. 9B.

Thus, the cellular invasion capability of tumor cells expressing HERV-H Env or Snail can be significantly reduced by inhibiting the expression of HERV-H Env or Snail. Therefore, function-inhibiting agents capable of inhibiting function of HERV-H Env are useful as antitumor agent.

Example 9

Function of HERV-H Env in Tumor Cell Expressing Endogenous HERV-H Env, and Suppression of the Function This example shows that HERV-H Env is involved in cell invasion of the tumor cells highly expressing endogenous HERV-H Env but not expressing Snail, and shows that invasion of colon tumor cells can be suppressed by inhibiting expression of HERV-H env gene.

First, cells from the human colon tumor cell line SW837 were transfected with siRNAs (SEQ ID NOs: 10 to 19) which specifically inhibit HERV-H env and the control oligonucleotides (SEQ ID NOs: 20 and 21) (Invitrogen Inc.) by the PEI complex method (Polyplus Inc.), and cultured for 2 to 3 days. It should be noted that SW837 is a cell line which expresses HERV-H Env but not Snail.

RT-PCR was conducted using the primers having the sequences of SEQ ID NOs: 6 to 9 and 26 to 35 as listed in Example 8 by following the "Method for Analyzing Gene Expression by RT-PCR" as described in Example 1 and expression of the genes of HERV-H env, Snail, Slug, Twist, E-cadherin, Fibronectin and GAPDH (as an internal standard) was examined.

Further, the human colon tumor cell line SW837 having been cultured for 2 to 3 days after the introduction of the siRNAs were recovered, and the number of cells whose cell membrane was invading into the lower surface (membrane invading cell number) was counted by following the "Method for Measuring Cellular Invasion Capability" as described in Example 1.

Figure 10:
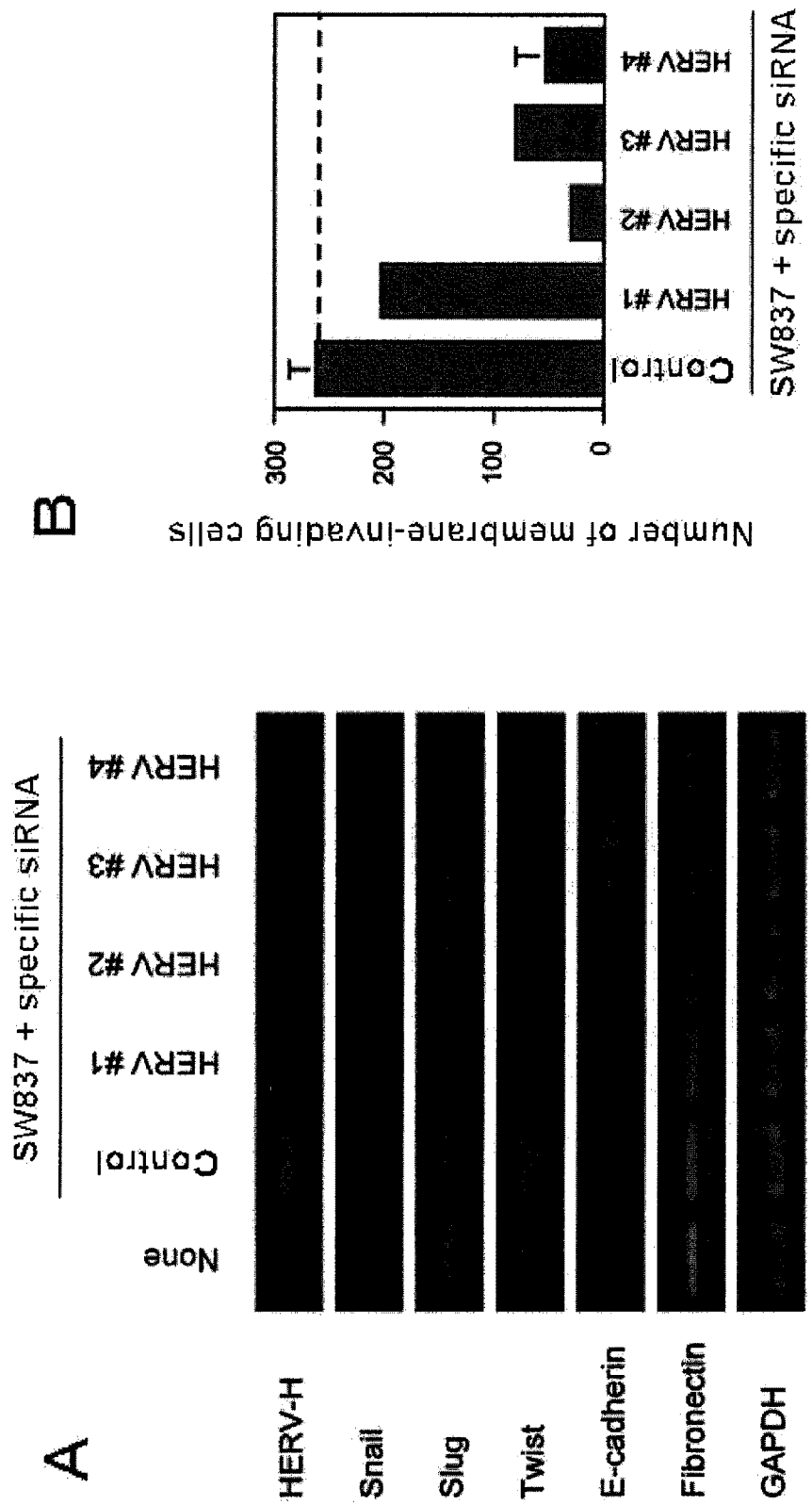
[FIG. 10]

As shown in FIG. 10A, the expression of HERV-H Env was detected in the siRNA non-transfected group (None), confirming that the SW837 cells were expressing endogenous HERV-H Env. In the cases where the expression of HERV-H env was inhibited by the siRNAs (HERV#1 to 4), the expression level of HERV-H env gene decreased, and at the same time, the expression levels of Slug, Twist and Fibronectin decreased, while the expression level of E-cadherin increased. Since these genes are known to control the epithelium-mesenchymal transition, the results indicate that malignancy of a tumor can be reduced by inhibiting the expression of HERV-H Env. Also, as shown in FIG. 10B, the number of membrane invading cells was lowered by the transfection with the siRNAs which inhibit expression of HERV-H env as compared to the control.

Thus, the cell invasion capability of tumor cells expressing HERV-H Env can be significantly reduced by inhibiting the expression of HERV-H Env. Therefore, function-inhibiting agents capable of inhibiting function of HERV-H Env are useful as antitumor agent.

Example 10

Function of HERV-H Env and Snail in Tumor Cells Expressing Endogenous HERV-H Env and Snail, and Suppression of the Function This example shows that HERV-H Env and Snail are involved in cell invasion of tumor cells expressing endogenous HERV-H Env and Snail, and shows that invasion of pancreatic tumor cells can be suppressed by inhibiting expression of HERV-H env gene or Snail gene.

First, cells of human pancreatic tumor cell line MIAPaca were transfected with siRNAs (SEQ ID NOs: 10 to 19) which specifically inhibit HERV-H env, siRNAs (SEQ ID NOs: 36 and 37) which specifically inhibit Snail (SiRNA-snail#2), and the control oligonucleotides (SEQ ID NOs: 20 and 21) (Invitrogen Inc.) by the PEI complex method (Polyplus Inc.), and cultured for 2 to 3 days. It should be noted that MIAPaca is a cell line which expresses both of endogenous HERV-H Env and Snail.

```
siRNA-snail#2:
Sense:
CCCACUCAGAUGUCAAGAAdTdT      (SEQ ID NO: 36)

Antisense:
UUCUUGACAUCUGAGUGGGdTdT      (SEQ ID NO: 37)
```

RT-PCR was conducted using the primers having the sequences of SEQ ID NOs: 6 to 9 and 26 to 35 as listed in Example 8 by following the "Method for Analyzing Gene Expression by RT-PCR" as described in Example 1 and expression of the genes of HERV-H env, Snail, Slug, Twist, E-cadherin, Fibronectin and GAPDH (as an internal standard) are examined.

Further, the human pancreatic tumor cell line MIAPaca having been cultured for 2 to 3 days after the introduction of the siRNAs were recovered, and the number of cells whose cell membrane was invading into the lower surface (membrane invading cell number) was counted by following the "Method for Measuring Cellular Invasion Capability" as described in Example 1.

Figure 11:
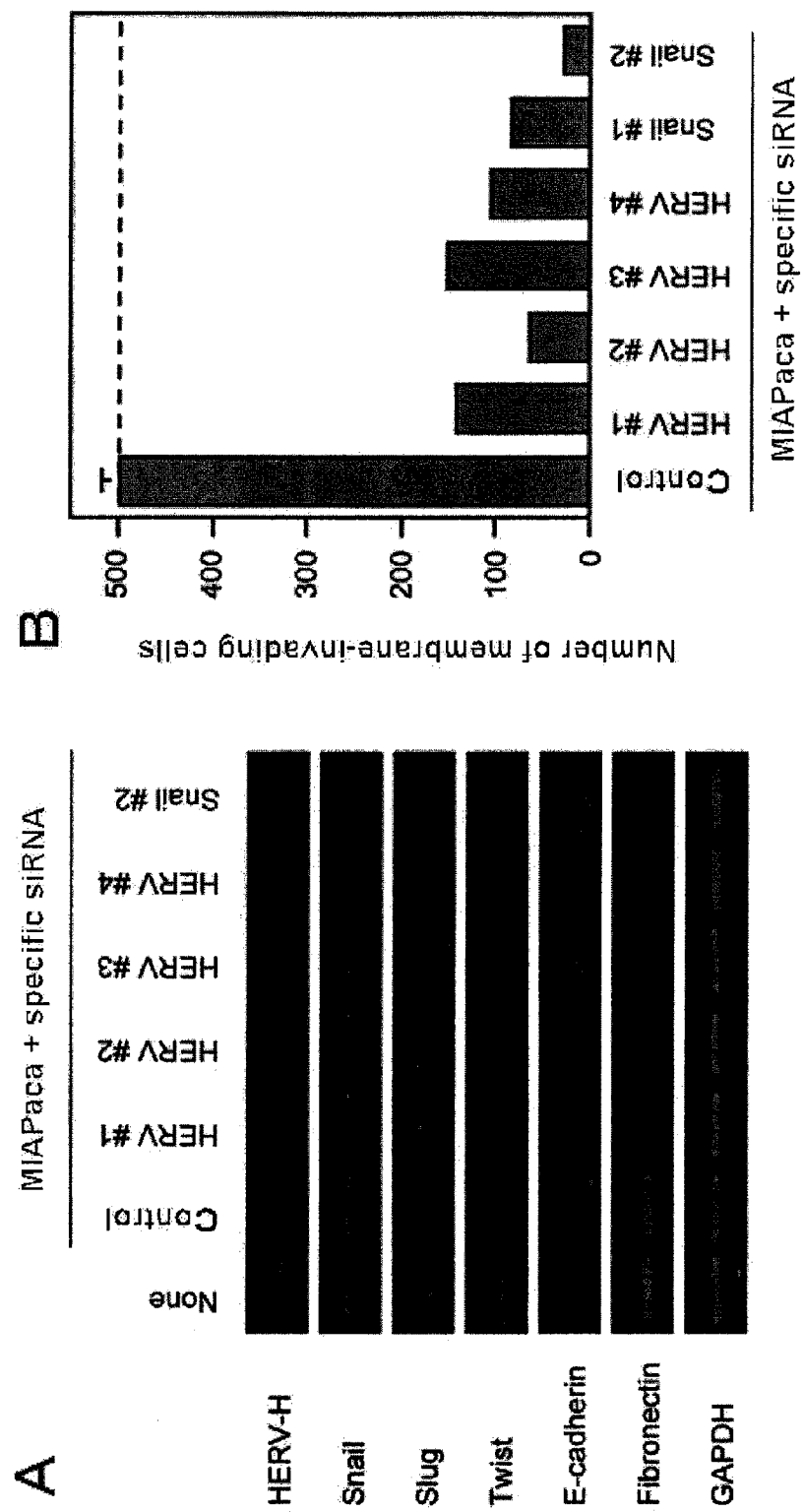
[FIG. 11]

As shown in FIG. 11A, the expression of HERV-H env and Snail was detected in the siRNS non-transfected group (None), confirming that the MIAPaca cells were expressing endogenous HERV-H Env and Snail. In the cases where the expression of HERV-H Env or Snail was inhibited by the siRNAs (HERV#1 to 4), the expression level of HERV-H env gene decreased, and at the same time, the expression levels of the genes known to control the epithelium-mesenchymal transition (Snail, Slug, Twist and Fibronectin) decreased, while the expression level of E-cadherin increased. These results indicate that malignancy of a tumor can be reduced by inhibiting the expression of HERV-H Env. Also, as shown in FIG. 11B, the number of membrane invading cells was lowered by the transfection with the siRNAs which inhibit expression of HERV-H env or Snail as compared to the control.

Thus, the cellular invasion capability of tumor cells expressing HERV-H Env or Snail can be significantly reduced by inhibiting the expression of HERV-H Env or Snail. Therefore function-inhibiting agents capable of inhibiting function of HERV-H Env are useful as antitumor agent.

[Industrial Applicability]

The present invention can provide methods for diagnosing and treating tumor, using HERV-H env gene or HERV-H Env protein; and more specifically, methods for diagnosing tumor by detecting expression of HERV-H env gene and a diagnosing agent to be used therein; methods for treating tumor by suppressing function of HERV-H env gene and antitumor agents to be used therein; methods for treating tumor by administering a peptide etc. including a certain sequence of HERV-H Env protein and cancer vaccines to be used therein.

The invention claimed is:

1. An isolated peptide consisting of any one of SEQ ID NOs: 3 to 5.

2. An isolated antigen-presenting cell presenting a peptide according to claim 1 on the cell surface.

3. A composition comprising a peptide according to claim 1, or an expression vector expressing a peptide according to claim 1.

4. A composition comprising a peptide of claim 1 and a tumor antigen peptide other than the peptide.

5. A composition comprising the isolated antigen-presenting cell according to claim 2.

* * * * *

SEQUENCE LISTING

```
<160> NUMBER OF SEQ ID NOS: 37

<210> SEQ ID NO 1
<211> LENGTH: 563
<212> TYPE: PRT
<213> ORGANISM: Homo sapiens
```

<400> SEQUENCE: 1

```
Met Ile Phe Ala Gly Arg Ala Ser Ser Asn Thr Ser Thr Leu Met Lys
1               5                   10                  15

Phe Tyr Ser Leu Leu Leu Tyr Ser Leu Leu Phe Ser Phe Pro Ile Leu
            20                  25                  30

Cys His Pro Leu Pro Leu Pro Ser Tyr Leu His His Thr Ile Asn Leu
        35                  40                  45

Thr His Ser Leu Leu Ala Val Ser Asn Pro Ser Leu Ala Lys Asn Cys
    50                  55                  60

Trp Leu Cys Ile Ser Leu Pro Ser Ser Ala Tyr Pro Ala Val Pro Ala
65                  70                  75                  80

Leu Gln Thr Asp Trp Gly Thr Ser Pro Val Ser Pro His Leu Arg Thr
                85                  90                  95

Ser Phe Asn Ser Pro His Leu Tyr Pro Pro Glu Lys Leu Ile Tyr Phe
            100                 105                 110

Leu Asp Arg Ser Ser Lys Thr Ser Pro Asp Ile Ser His Gln Gln Ala
        115                 120                 125

Ala Ala Leu Leu Cys Thr Tyr Leu Lys Asn Leu Ser Pro Tyr Ile Asn
    130                 135                 140

Ser Thr Pro Pro Thr Phe Gly Pro Leu Thr Thr Gln Thr Thr Ile Pro
145                 150                 155                 160

Val Ala Ala Pro Leu Cys Ile Ser Arg Gln Arg Pro Thr Gly Ile Pro
                165                 170                 175

Leu Gly Asn Leu Ser Pro Ser Arg Cys Ser Phe Thr Leu His Leu Arg
            180                 185                 190

Ser Pro Thr Thr His Ile Thr Glu Thr Asn Gly Ala Phe Gln Leu His
        195                 200                 205

Ile Thr Asp Lys Pro Ser Ile Asn Thr Asp Lys Leu Lys Asn Val Ser
    210                 215                 220

Ser Asn Tyr Cys Leu Gly Arg His Leu Ser Cys Ile Ser Leu His Pro
225                 230                 235                 240

Trp Leu Phe Ser Pro Cys Ser Ser Asp Ser Pro Arg Pro Ser Ser
                245                 250                 255

Cys Leu Leu Ile Pro Ser Pro Lys Asn Asn Ser Glu Ser Leu Leu Val
            260                 265                 270

Asp Ala Gln Arg Phe Leu Ile Tyr His Glu Asn Arg Thr Ser Pro Ser
        275                 280                 285

Thr Gln Leu Pro His Gln Ser Pro Leu Gln Pro Leu Thr Ala Ala Pro
    290                 295                 300

Leu Gly Gly Ser Leu Arg Val Trp Val Gln Asp Thr Pro Phe Ser Thr
305                 310                 315                 320

Pro Ser His Leu Phe Thr Leu His Leu Gln Phe Cys Leu Val Gln Ser
                325                 330                 335

Leu Phe Phe Leu Cys Gly Ser Ser Thr Tyr Met Cys Leu Pro Ala Asn
            340                 345                 350

Trp Thr Gly Thr Cys Thr Leu Val Phe Leu Thr Ser Lys Ile Gln Phe
        355                 360                 365

Ala Asn Gly Thr Glu Glu Leu Pro Val Pro Leu Met Thr Pro Thr Arg
    370                 375                 380

Gln Lys Arg Val Ile Pro Leu Ile Pro Leu Met Val Gly Leu Gly Leu
385                 390                 395                 400

Ser Ala Ser Thr Val Ala Leu Gly Thr Gly Ile Ala Gly Ile Ser Thr
                405                 410                 415
```

-continued

```
Ser Val Thr Thr Phe Arg Ile Leu Ser Asn Asp Phe Ser Ala Ser Ile
            420                 425                 430

Thr Asp Ile Ser Gln Thr Leu Ser Gly Leu Gln Ala Gln Val Asp Ser
        435                 440                 445

Ser Ala Val Val Leu Gln Asn Arg Gln Gly Leu Asp Leu Leu Thr
450                 455                 460

Ala Glu Lys Gly Gly Leu Cys Ile Phe Leu Asn Glu Glu Ser Tyr Phe
465                 470                 475                 480

Tyr Leu Asn Gln Ser Gly Leu Val Tyr Asp Asn Ile Lys Lys Leu Lys
                485                 490                 495

Asp Lys Ala Gln Asn Leu Ala Asn Gln Ala Ser Asn Tyr Ala Glu Pro
                500                 505                 510

Pro Trp Pro Leu Ser Asn Trp Met Ser Trp Val Leu Pro Ile Leu Ser
            515                 520                 525

Pro Leu Ile Pro Ile Phe Leu Leu Leu Phe Phe Arg Pro Cys Ile Phe
        530                 535                 540

His Leu Val Ser Gln Phe Ile Gln Asn His Ile Gln Ala Ile Thr Asp
545                 550                 555                 560

His Ser Ile
```

<210> SEQ ID NO 2
<211> LENGTH: 7884
<212> TYPE: DNA
<213> ORGANISM: Homo sapiens

<400> SEQUENCE: 2

| | |
|---|---:|
| atgaaatatt actgtgtcaa catagaaata cagagtagtc aaataaattg ttagtgtttc | 60 |
| attttatatt ctgtgaagtc tgttttataa tcagcagaga caccaaattc atgatgtgtc | 120 |
| agaatcattt ctattttatt tcaaatgcta tttaatatca ataaaaataa aaacaaaggt | 180 |
| ataataaaat ataatagctt gatttccttg tattctgtcc ttgttcctta atttcaatgc | 240 |
| aaattacatt tcaactcctg atgatattca gttattttg ttctccaaat atgtcaggcc | 300 |
| tctgagccca agccaagcca ttgcatcccc tgtgacttgc acgtatacat ccagatggcc | 360 |
| tgaagtaact gaagatccac aaaagaagta aaaacagcct taactgatga cattccacca | 420 |
| ttgtgatctg ttcgtgcccc accctaactg atcaatctcc cccacccta agaaggtact | 480 |
| ctaattctcc ccaccttga gaatgtactt tgtgagatcc acccctgccc tcaaaacatt | 540 |
| gctcttaact tcaccaccta tcccaaaacc tataagaact aatgataatc caccacccctt | 600 |
| tgctgactct cttttggac tcagcccacc tgcacccagg tgaaataaac agctttattg | 660 |
| ctcacacaaa gcctgtttgg tggtcttttc acatggacgc acatgaaatt tggtgccgtg | 720 |
| actcggatcg ggggacctcc cttgggagat aaatcccctg tcctcctgct ctttgctcca | 780 |
| tgagaaaaga tccacctatg acctcaggtc ctcagactga ccagcccaag aaacatctca | 840 |
| ccaatttaaa atccggtaag cggcctcttt ttactctctt ctccaacttc cctcactatc | 900 |
| cctcaacctc tttctccttt caatcttggc accacacttc aatctctccc ttctcttaat | 960 |
| ttcaattcct ttcattttct ggtagagaca aaggagacat gttttatccg tggacccaaa | 1020 |
| actccggcgc cagtcacgga ctgggaaggc agccttccct tggtgtttaa tcattgcaag | 1080 |
| gatgcctctc tgattattca cccaggtttc aaaggtgtca gaccacacag ggacgcctgc | 1140 |
| cttggtcctt caccttagc ggcaagtccc gcttttctgg ggaagggcaa gtacccaac | 1200 |
| tccttctctc catgtctcta cctcttctct gctttcctgg gggtggggca agtacccctc | 1260 |
| aaccccttct ccttcacccct tagcggcaag tcccactttt ctagggggtca agaaccccca | 1320 |

```
atcccttatt tccgtgccct gacccctttc ctactttcct ggagggtaag aaccccaaa    1380
ccccttccct ccatgtctct actctctctt ttctctgggc ttgcctcctt cactgtgggc    1440
aaccttccac cctccattct tcctccttct cccttagcct gtgttcttaa gaacttaaaa    1500
cctcttcaac tctcacctga cctaaaatct aagcatcttg ttttcttctg caatgccagt    1560
tgacccaat  acaaactcaa cagtagttcc aaatagccag aaaatggcac tttcaatttt    1620
tccatcctgc aagatctaaa taattcttgt cgtaaaatgg caaaggtc   tgaggtgcct    1680
gacttcccgg cattctttta cacattggtc cctccctagt ctctgtgtcc agtgcaactc    1740
gtcccaaatc ttcttccttc tttccctcct gccagtcccc tcagtcccaa cccgaagcat    1800
tgctgagtct ttctaatctt ccttttccac agacccatct gacctctccc ctcctcgcca    1860
ggctgagcta agtcccaatt cttcctcagc ctctgctcct ccaccctata tccttttat    1920
cacctcccct cctcacacct ggtcccactt acagtttcat accatgacta gccctccccc    1980
acctgcccag caattactc  ttaaaaaggt ggctggagct aaaggcataa tcaaggttaa    2040
tgctccttt  tctttatccc aaatcagata gcatttaggc tcttttcat  caaatataaa    2100
atccagccca gttcatggct cgtttggcag cgacccgaa  acgctttaca gccctagacc    2160
ctaaaaggtc aaaaggccgt cttattctca aaatacattt tattacccaa tctgctcctg    2220
acattaaata aaactccaaa aaattaaatt ccggccctca aacccacaa  caggattcaa    2280
ttaacctcgc cttcaaggtg tacaataata gaaaaagtt  gcaattactt gcctccactg    2340
tgagacaaac cccagccaca tctccagcac acaagaactt ccaaacacct gaaccgcagc    2400
agccaggcat tcctccagaa cctcctcccc caggagcttg ctacaagtgc cagaaatctg    2460
accaccaggc caaggaatgc ctatagccca ggattcctcc taagccatgt cgcatctttg    2520
cgggacccca ctggaaatca gactgttcaa ctcacctggc agctactccc agagcctctg    2580
gaactctggc ccaaggctct ctgacggact ccttctcggt ttagcggctg aagactgatg    2640
ctgcccgatc acctcggaac cccgtagac  catcacggac gccgagtttc gggtaactct    2700
cacagtggaa ggtaagtcca tccccttagt caatacagag gctacccact ccacattacc    2760
ttctttcaa  gggcctgttt cccttgcccc cataactgtt gtgggtattg acggccaggc    2820
ttctaaaccc ctgaaaactc ccccactctt gtgccaactt ggacaacact cttttatgca    2880
ctctttttta gttatcccca cctgcccagt tcacttatta ggccaaaata ttttaaccaa    2940
atcatctgct tccctgacta ttcctggact acagccgcat ctcattgctg cacttcttcc    3000
caacccaaag cctcctttgc gtcttcctct cctatccccc caccttaacc cacaagtatg    3060
ggacatctct actccttccc ttgcaaccga tgacatgccc attaccatca catgtccatt    3120
accatctcat taaaacctaa tcactcttac ctggctcaac gccaatatcc catccaacag    3180
cattgcttta aaaggattaa agccaggccg ggcgcggtgg ctcacgcctg taatcccagc    3240
actttgggag gccgaggcgg gtggatcatg aggtcaggag atcgagacca tcctggctaa    3300
caaggtgaaa ccccgtctct actaaaaata caaaaaatta gccgggcgcg gtggcgggcg    3360
cctgtggtcc cagctactcg ggaggctgag gcaggagaat ggcgtgaacc cgggaagcgg    3420
agcttgcagt gagccgagat tgcgccactg cagtcccgca accccggcct gggcgacaga    3480
gcgagactcc gtctcttaaa aaaaaaaaa  ggattaaagc ctgttaccac ccgcctgcta    3540
cagcatgggc ttctaaaacc tataaactct ccttacaatt tccccatttt acctgtccaa    3600
aaaccggaca agtcttacag attagttcag gatctgcacc ttatcaacca aattgttttg    3660
cctatccacc ctgtagtgcc caacccgtac actcttctgt cctcaatacc ttcctccaca    3720
```

```
actcactatt ccgttctcga tcttaaagat gcttttttta ctattcccct gcacgcctca   3780
tcccagatct ctttgctttc acttagactg accctgacac ccattaggtt cagcaaatta   3840
cctgggctgt actgccgcaa gtcttcatag acagccccca ttacttcagt caagctcaaa   3900
tttcatcctc atctgttacc tatctcggca caattctcat aaaaacacgt gctttccctg   3960
ctgattgtgt ccgattaatc tcccaaacct caatccctta caaaacaaca actccttccc   4020
ttcctaggca tagtgcagtc agaattctta caaaagagcc aggaccacac cctatagcct   4080
ttctgtccaa acaacttgac cttactgttt tagcctagcc atcatgtctc cctgcagcgg   4140
ctgctgccac cctaatactt ttagaggccc tcaaaatcac aaactatgct caacttactc   4200
tctacatttc tcataacttc caaaatctat tttcttcctc atacctgatg catatacttt   4260
ctgctccccg gctccttcag ctgtactcac tctttgttaa gtcccacaat taccattgtt   4320
cctgaccggg acttcaatcc ggtctcccac attattctgg aaaccacacc tgaccctcat   4380
gactgtatct ctctgatcca cctgacattc acctcatttc cccatatttc cttctttcct   4440
gttcctcacc ctgatcatgc ttgatttatt aatggcggtt ccaccaggcc taatcaccac   4500
acaccagcaa aggcaggcta tgctatagta cacatcacta gcccgcctct taaaacctct   4560
catttccttt ccatcgtgga aatctatcct caaggaaata acttctcagt gttccatctg   4620
ctattctact actcctcagg gattattcag gcccctgcc ttccctacac atcaagctcg    4680
agaatttgcc cccacccagg actggcaaat tagctttact caacatgccc cgagtcagaa   4740
aactaaaata cctcttagtc taggtagaca ctttcactgg ataggtagag cctttcctta   4800
cagggtctga gaaggccacc acagtcattt cttcccttct gtcagacata atccctcagt   4860
ttagccttcc cacctctata cagtctgata actgaccagc ctttattagt caaatcagcc   4920
aagcagtttt tcaggctctt aatatttagt gaaacctta tatcccttac agtcctcagt    4980
cttcaggaaa agtagaacag actaacggtc ttttaaaaac acacctcacc aagctcagcc   5040
accaacttaa aaaggactag acaatacttt taccactttc ctttctcaga agtcagacct   5100
gtcctcagaa tgctacaggg tacagcccat ttgagctcct gtatagatgc tcctttttat   5160
taggccccag tctcattcca gagagcagac taacttagac tgtgccccca aaaacgagtc   5220
atccctacta tcttctgtct ggtcatactc ctattctcca ttatcaacta cttataaatg   5280
ccctactctt gtttacacca ccggtttaca ctgtttcttc aagccatcac agctgatatc   5340
tcttggtgct atcccgaaac tgccactctt aactccctct tagagtggat agatgatctt   5400
tgctggcagg gcatcctcca atacttccac cctgatgaag ttctattctt tacttttata   5460
ctcactctta ttctcattcc caatcttatg ccacccttta cctctcccca gctatctcca   5520
ccacactatc aaccttaccc attctctcct agccgtttct aatccctcct tagcgaaaaa   5580
ctgctggctt tgcatttccc ttccttccag tgcctaccca gctgtccctg ccttacagac   5640
agactgggga acatctcctg tctccccaca cctccgaact tcctttaaca gccctcacct   5700
ttaccctcct gaaaaactca tttactttct agacaggtcc agcaagactt ccccagacat   5760
ttcacatcag caagctgccg ccctcctctg cacttattta aaaaaccttt ctccttatat   5820
taactctact cccccacat ttggaccgct cacaacacaa actactattc ctgtggccgc    5880
tccttttatgt atctctcggc aaagacccac tggaattccc ctaggtaatc tttcaccttc   5940
tcgatgttcc tttactcttc atctccgaag cccaactaca cacatcactg aaacaaatgg   6000
agccttccag ctccatatta cagacaagcc ctctatcaat actgacaaac ttaaaaacgt   6060
tagcagtaat tattgcttag gaagacactt gtcctgtatt tcactccatc cttggctatt   6120
```

-continued

```
ttcccccttgc tcatcagact ctcctcccag accctcttct tgtttactta tacccagccc      6180
caaaaataac agtgaaagtt tgctcgtaga tgctcaacgt tttctcatat accatgaaaa      6240
tcgaacctcc ccctctacgc agttacccca tcagtcccca ttacaacctc tgactgctgc      6300 cccccctaggt ggatccctaa gagtctgggt acaagacacc cctttcagca ctccttctca      6360
cctttttact ttacatctcc agttttgcct agtacaaagt ctcttcttcc tctgtggatc      6420
ctctacctac atgtgtctac ctgctaattg gacaggcaca tgcacactag ttttccttac      6480
ctccaaaatt caatttgcaa atgggactga agagctccct gttccctca tgacaccgac      6540 acgacaaaaa agagttattc cactaattcc cttgatggtt ggtttaggac tttctgcctc      6600
cactgttgct ctcggtactg aatagcagg catttcaacc tccgtcacga ccttccgtat      6660
cctgtctaat gacttctctg ctagcattac agacatatca caaactttat caggcctcca      6720
ggcccaagtt gactcttcag ctgcagttgt cctccaaaac cgccaaggcc ttgacttact      6780
cactgctgaa aaggaggac tctgtatatt cttaaatgaa gagtcttatt tttacctaaa      6840
tcaatctggc ctggtgtatg acaacataaa aaaactcaag gataaagccc aaaatcttgc      6900
caaccaagca agtaattatg ctgaaccccc ttggccactc tctaattgga tgtcctgggt      6960
ccttccaatt cttagtcctt taatacccat ttttctcctt ctttttttca gaccttgtat      7020
cttccattta gtttctcaat tcatccaaaa ccatatccag gccatcaccg atcattctat      7080
atgacaaatg tttcttctaa catccccaca atatcaccac ttaccacaag atctcccttc      7140
agcttaatct ctcccactct aggttcccac accgccccta atcccgcttg aagcagccct      7200
gagaaacatc gcccattctc tctctcacac cacccccccaa aaatttcgcc gccccaacac      7260
ttcaacacta ttttgtttta tttttcttat taatataaga aggcaggaat gtcaggcctc      7320
tgagcccaag ccaagccatc gcatctcctg tgacttgcat gtatacatcc agatggtctg      7380
aagtaactga agatccacaa aagaagtaaa aatagcctta actgatgaca ttccaccact      7440
gtgatttgtt cctgccccac cctaactgat caatgtactt tgtaatctcc cccaccctta      7500
agaaggtact ttgtaattct ccccacccct gagaatgtac tttgtgagat ccaccccctgc      7560 ctgcaaaaca ttgctcttaa cttcaccacc tatcctaaaa cctataagaa ctaatgatga      7620
tccaccaccc tttgctgact ctcttttcag actcagccca cctgcaccca ggtgaaataa      7680
acagctttat tgctcacaca aagcctgttt ggtggtctct tcacacggac gcgcatgaaa      7740
aaatatacta tctgaattta acaaactatt gctaaatttt ttgaaataaa ttttaaata      7800 cttttctcatt ttgtaccaaa agtacaaatt ttacaaaatg atttatgatt ttaataatta      7860
ctactaacaa acatttttta agga                                            7884
```

<210> SEQ ID NO 3
<211> LENGTH: 9
<212> TYPE: PRT
<213> ORGANISM: Homo sapiens

<400> SEQUENCE: 3

Ser Tyr Leu His His Thr Ile Asn Leu
1               5

<210> SEQ ID NO 4
<211> LENGTH: 9
<212> TYPE: PRT
<213> ORGANISM: Homo sapiens

<400> SEQUENCE: 4

```
Phe Tyr Ser Leu Leu Leu Tyr Ser Leu
1               5

<210> SEQ ID NO 5
<211> LENGTH: 9
<212> TYPE: PRT
<213> ORGANISM: Homo sapiens

<400> SEQUENCE: 5

Asn Tyr Ala Glu Pro Pro Trp Pro Leu
1               5

<210> SEQ ID NO 6
<211> LENGTH: 22
<212> TYPE: DNA
<213> ORGANISM: Homo sapiens

<400> SEQUENCE: 6
ggatcctcta cctacatgtg tc                                              22

<210> SEQ ID NO 7
<211> LENGTH: 22
<212> TYPE: DNA
<213> ORGANISM: Homo sapiens

<400> SEQUENCE: 7
tcaagggaat tagtggaata ac                                              22

<210> SEQ ID NO 8
<211> LENGTH: 21
<212> TYPE: DNA
<213> ORGANISM: Homo sapiens

<400> SEQUENCE: 8
gtcaacggat ttggtcgtat t                                               21

<210> SEQ ID NO 9
<211> LENGTH: 21
<212> TYPE: DNA
<213> ORGANISM: Homo sapiens

<400> SEQUENCE: 9
atcactgcca cccagaagac t                                               21

<210> SEQ ID NO 10
<211> LENGTH: 21
<212> TYPE: DNA
<213> ORGANISM: Artificial Sequence
<220> FEATURE:
<223> OTHER INFORMATION: siRNA

<400> SEQUENCE: 10
ccaaucuuau gccacccuut t                                               21

<210> SEQ ID NO 11
<211> LENGTH: 21
<212> TYPE: DNA
<213> ORGANISM: Artificial Sequence
<220> FEATURE:
<223> OTHER INFORMATION: siRNA

<400> SEQUENCE: 11 aagggguggca uaagauuggt t                                              21

<210> SEQ ID NO 12
```

```
<211> LENGTH: 21
<212> TYPE: DNA
<213> ORGANISM: Artificial Sequence
<220> FEATURE:
<223> OTHER INFORMATION: siRNA

<400> SEQUENCE: 12
ccaauucuua guccuuuaat t                                              21

<210> SEQ ID NO 13
<211> LENGTH: 21
<212> TYPE: DNA
<213> ORGANISM: Artificial Sequence
<220> FEATURE:
<223> OTHER INFORMATION: siRNA

<400> SEQUENCE: 13
uuaaaggacu aagaauuggt t                                              21

<210> SEQ ID NO 14
<211> LENGTH: 21
<212> TYPE: DNA
<213> ORGANISM: Artificial Sequence
<220> FEATURE:
<223> OTHER INFORMATION: siRNA

<400> SEQUENCE: 14
ccaggccauc accgaucaut t                                              21

<210> SEQ ID NO 15
<211> LENGTH: 21
<212> TYPE: DNA
<213> ORGANISM: Artificial Sequence
<220> FEATURE:
<223> OTHER INFORMATION: siRNA

<400> SEQUENCE: 15
augaucggug auggccuggt t                                              21

<210> SEQ ID NO 16
<211> LENGTH: 21
<212> TYPE: DNA
<213> ORGANISM: Artificial Sequence
<220> FEATURE:
<223> OTHER INFORMATION: siRNA

<400> SEQUENCE: 16
ggaggacucu guauauucut t                                              21

<210> SEQ ID NO 17
<211> LENGTH: 21
<212> TYPE: DNA
<213> ORGANISM: Artificial Sequence
<220> FEATURE:
<223> OTHER INFORMATION: siRNA

<400> SEQUENCE: 17
agaauauaca gaguccucct t                                              21

<210> SEQ ID NO 18
<211> LENGTH: 21
<212> TYPE: DNA
<213> ORGANISM: Artificial Sequence
<220> FEATURE:
<223> OTHER INFORMATION: siRNA

<400> SEQUENCE: 18
```

```
gcgagcugca ggacucuaat t                                              21

<210> SEQ ID NO 19
<211> LENGTH: 21
<212> TYPE: DNA
<213> ORGANISM: Artificial Sequence
<220> FEATURE:
<223> OTHER INFORMATION: siRNA

<400> SEQUENCE: 19
uuagaguccu gcagcucgct t                                              21

<210> SEQ ID NO 20
<211> LENGTH: 21
<212> TYPE: DNA
<213> ORGANISM: Artificial Sequence
<220> FEATURE:
<223> OTHER INFORMATION: siRNA

<400> SEQUENCE: 20
ggaucagucu auuaggucut t                                              21

<210> SEQ ID NO 21
<211> LENGTH: 21
<212> TYPE: DNA
<213> ORGANISM: Artificial Sequence
<220> FEATURE:
<223> OTHER INFORMATION: siRNA

<400> SEQUENCE: 21
agaccuaaua gacugaucct t                                              21

<210> SEQ ID NO 22
<211> LENGTH: 9
<212> TYPE: PRT
<213> ORGANISM: Homo sapiens

<400> SEQUENCE: 22

Leu Tyr Lys Pro Asp Ser Asn Glu Phe
1               5

<210> SEQ ID NO 23
<211> LENGTH: 9
<212> TYPE: PRT
<213> ORGANISM: Homo sapiens

<400> SEQUENCE: 23

Leu Leu Met Trp Ile Thr Gln Cys Phe
1               5

<210> SEQ ID NO 24
<211> LENGTH: 9
<212> TYPE: PRT
<213> ORGANISM: Homo sapiens

<400> SEQUENCE: 24

Thr Tyr Ala Cys Phe Trp Ser Asn Leu
1               5

<210> SEQ ID NO 25
<211> LENGTH: 9
<212> TYPE: PRT
<213> ORGANISM: Homo sapiens

<400> SEQUENCE: 25

Cys Met Thr Trp Asn Gln Met Asn Leu
```

<210> SEQ ID NO 26
<211> LENGTH: 22
<212> TYPE: DNA
<213> ORGANISM: Artificial Sequence
<220> FEATURE:
<223> OTHER INFORMATION: primer

<400> SEQUENCE: 26
cagatgagga cagtgggaaa gg                                               22

<210> SEQ ID NO 27
<211> LENGTH: 22
<212> TYPE: DNA
<213> ORGANISM: Artificial Sequence
<220> FEATURE:
<223> OTHER INFORMATION: primer

<400> SEQUENCE: 27
actcttggtg cttgtggagc ag                                               22

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
agcgaactgg acacacatac                                                  20

<210> SEQ ID NO 29
<211> LENGTH: 19
<212> TYPE: DNA
<213> ORGANISM: Artificial Sequence
<220> FEATURE:
<223> OTHER INFORMATION: primer

<400> SEQUENCE: 29
tctagactgg gcatcgcag                                                   19

<210> SEQ ID NO 30
<211> LENGTH: 25
<212> TYPE: DNA
<213> ORGANISM: Artificial Sequence
<220> FEATURE:
<223> OTHER INFORMATION: primer

<400> SEQUENCE: 30
gcaagcttag agatgatgca ggacg                                            25

<210> SEQ ID NO 31
<211> LENGTH: 26
<212> TYPE: DNA
<213> ORGANISM: Artificial Sequence
<220> FEATURE:
<223> OTHER INFORMATION: primer

<400> SEQUENCE: 31
gactcgaggt gggacgcgga catgga                                           26

<210> SEQ ID NO 32
<211> LENGTH: 30
<212> TYPE: DNA
<213> ORGANISM: Artificial Sequence
<220> FEATURE:

```
<223> OTHER INFORMATION: primer

<400> SEQUENCE: 32
ttcctcccaa tacatctccc ttcacagcag                                    30

<210> SEQ ID NO 33
<211> LENGTH: 30
<212> TYPE: DNA
<213> ORGANISM: Artificial Sequence
<220> FEATURE:
<223> OTHER INFORMATION: primer

<400> SEQUENCE: 33
cgaagaaaca gcaagagcag cagaatcaga                                    30

<210> SEQ ID NO 34
<211> LENGTH: 17
<212> TYPE: DNA
<213> ORGANISM: Artificial Sequence
<220> FEATURE:
<223> OTHER INFORMATION: primer

<400> SEQUENCE: 34
ccgtgggcaa ctctgtc                                                  17

<210> SEQ ID NO 35
<211> LENGTH: 17
<212> TYPE: DNA
<213> ORGANISM: Artificial Sequence
<220> FEATURE:
<223> OTHER INFORMATION: primer

<400> SEQUENCE: 35
tgcggcagtt gtcacag                                                  17

<210> SEQ ID NO 36
<211> LENGTH: 21
<212> TYPE: DNA
<213> ORGANISM: Artificial Sequence
<220> FEATURE:
<223> OTHER INFORMATION: siRNA

<400> SEQUENCE: 36
cccacucaga ugucaagaat t                                             21

<210> SEQ ID NO 37
<211> LENGTH: 21
<212> TYPE: DNA
<213> ORGANISM: Artificial Sequence
<220> FEATURE:
<223> OTHER INFORMATION: siRNA

<400> SEQUENCE: 37
uucuugacau cugagugggt t                                             21
```